United States Patent [19]

Kalopissis et al.

[11] 4,009,255

[45] Feb. 22, 1977

[54] HAIR TREATING COMPOSITIONS CONTAINING CATIONIC SURFACE ACTIVE AGENTS

[75] Inventors: Gregoire Kalopissis, Paris; Guy Vanlerberghe, Mitry-Mory, both of France

[73] Assignee: Societe Anonyme dite: L'Oreal, Paris, France

[22] Filed: Feb. 6, 1975

[21] Appl. No.: 547,465

Related U.S. Application Data

[60] Division of Ser. No. 187,151, Oct. 6, 1971, Pat. No. 3,879,464, which is a continuation-in-part of Ser. No. 655,336, July 24, 1967, abandoned.

[30] Foreign Application Priority Data

July 26, 1966 Luxembourg .......................... 51645
May 12, 1967 Luxembourg .......................... 53667

[52] U.S. Cl. .................................... 424/70; 8/10; 8/10.1; 8/10.2; 8/11; 8/32; 252/544; 252/547; 260/293.83; 260/293.9; 260/297 R; 260/567.6 M; 260/570.5 R; 260/583 R; 260/584 B; 260/584 C; 260/247.7 Z; 424/DIG. 2; 424/71; 424/72

[51] Int. Cl.[2] .................................... A61K 7/06

[58] Field of Search ... 424/70; 260/583 R, 570.5 R, 260/584 C, 584 B, 247.7 A, 567.6 M, 247.7 C, 293.83, 293.9, 297; 252/DIG. 13, 544, 547

[56] References Cited

UNITED STATES PATENTS

| | | | |
|---|---|---|---|
| 3,155,591 | 11/1964 | Hilfer | 424/70 |
| 3,206,512 | 9/1965 | Koebner et al. | 424/70 X |
| 3,272,712 | 9/1966 | Kalopissis et al. | 424/70 |
| 3,449,430 | 6/1969 | Dohr et al. | 260/583 R |

*Primary Examiner*—Albert T. Meyers
*Assistant Examiner*—Vera C. Clarke
*Attorney, Agent, or Firm*—Cushman, Darby & Cushman

[57] ABSTRACT

Cationic surface-active agents which are polyhydroxylated tertiary amines or the quaternary ammonium salts thereof and which are usefully employed in cosmetic compositions, are prepared by condensing on a fatty alcohol, glycerol epihalohydrin alone or together with an epoxide to form polyhalogenated polyethers, which in turn are converted to polyhalogenated glycidyl ethers, the latter being reacted with a secondary amine to form polyhalogenated tertiary amines which are then reacted with sodium or potassium acetate in the presence of a diol to form said polyhydroxylated tertiary amines.

19 Claims, No Drawings

HAIR TREATING COMPOSITIONS CONTAINING CATIONIC SURFACE ACTIVE AGENTS

This application is a division of application Ser. No. 187,151, filed Oct. 6, 1971, now U.S. Pat. No. 3,879,464 which is a continuation-in-part of application Ser. No. 655,336, filed July 24, 1967, now abandoned.

The present invention relates to cationic surface active agents which are the condensation products of an alcohol having the formula ROH with (a) glycerol epihalohydrin or (b) an epoxide and glycerol epihalohydrin.

I. Surface Active Agents Which Are The Condensation Product Of An Alcohol And Glycerol Epihalohydrin In accordance with this embodiment of the present invention there are provided cationic surface active agents selected from the group consisting of 1. agents having the formula

which are hydroxylated condensation products of an alcohol having the formula ROH and glycerol epihalohydrin wherein R is a hydrophilic group selected from the class consisting of linear or branched alkyl and alkenyl having 8-22 carbon atoms, and alkylphenyl having 8-22 carbon atoms, $R_1$ and $R_2$ each independently are selected from the group consisting of lower alkyl having 1-4 carbon atoms and hydroxy lower alkyl having 1-4 carbon atoms or together with the nitrogen atom to which they are attached form a ring selected from the group consisting of morpholine and piperidine and $n$ is 0.5–10; and 2. agents which are the quaternary ammonium salts of (1) having the formula

where $n$, R, $R_1$ and $R_2$ have the meaning given above, $R_3$ is selected from the group consisting of methyl and ethyl, and Y is an anion selected from the group consisting of Cl, Br, I, $SO_4CH_3$, $SO_4C_2H_5$, $CH_3SO_3$ and

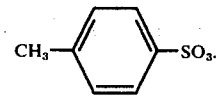

The cationic surface active agents of this embodiment of the invention are prepared by a. condensing on a fatty alcohol or on an alkyl phenol having the formula ROH wherein R has the meaning given above $(n+1)$ moles of glycerol epihalohydrin having the formula

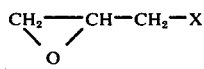

wherein $n$ has the meaning given above and X is halogen, preferably chlorine or bromine to form a mixture of polyhalogenated polyethers having the formula
$$RO-[C_2H_3(CH_2X)O]_n CH_2-CHOH-CH_2X \quad (III);$$

b. dehydrohalogenating said polyhalogenated polyethers from step (a) with an alkali metal hydroxide or an alkaline earth metal hydroxide to form a mixture of polyhalogenated glycidyl ethers having the formula

c. reacting the polyhalogenated glycidyl ethers from step (b) with a secondary amine to form a mixture of polyhalogenated tertiary amines having the formula

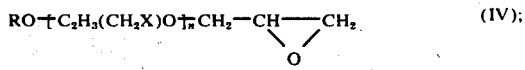

and d. replacing the halogen by a hydroxyl in the polyhalogenated tertiary amines from step (c) to form a mixture of polyhydroxylated tertiary amines having (II)

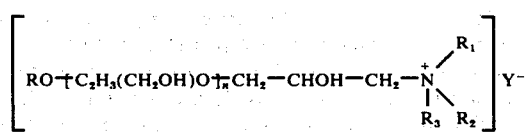

formula (I) given above.

The various steps in the above process for preparing the surface active agents represented by formula (I) are as follows:

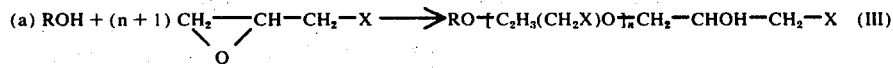

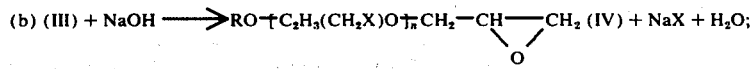

(c) $(IV) + HN\begin{matrix}R_1\\ \\R_2\end{matrix} \longrightarrow RO\text{---}[C_2H_3(CH_2X)O]_{\overline{n}}CH_2\text{---}CHOH\text{---}CH_2\text{---}N\begin{matrix}R_1\\ \\R_2\end{matrix}$ (V); and (d) $(V) \xrightarrow[+OH]{-X} RO\text{---}[C_2H_3(CH_2OH)O]_{\overline{n}}CH_2\text{---}CHOH\text{---}CH_2\text{---}N\begin{matrix}R_1\\ \\R_2\end{matrix}$ (I).

The quaternization of the surface active agents represented by formula I yields quaternary ammonium salts having the formula

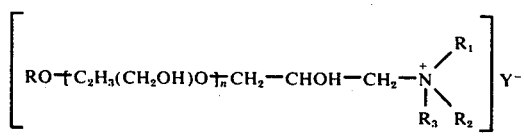

(II)

wherein R, $R_1$, $R_2$, $R_3$, $Y^-$ and n have the meaning given above.

In the course of the condensation reaction (a) above, when the epoxy ring is opened during the polycondensation, a mixture of compounds comprising the structures

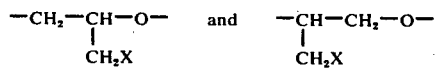

is obtained.

Thus a mixture of compounds having the general structure —$C_2H_3(CH_2X)O$— is obtained. Consequently, the hydroxylated compound of formula I and II given above represents the two isomers

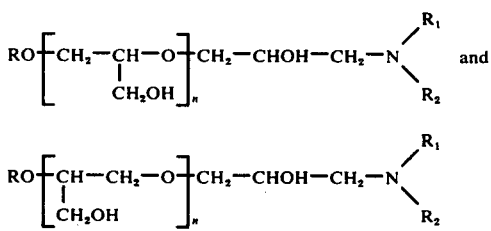

and the corresponding two isomers of the quaternary ammonium salts.

In the above formulae n is defined by the equation:

$$(n + 1) = \frac{56,000 - IM}{IE}$$

wherein M is equal to the molecular weight of the alcohol or alkyl phenol ROH, E is equal to the molecular weight of the glycerol epihalohydrin and I is the hydroxyl index of the condensation product, i.e., the mixture of polyhalogenated polyethers represented by formula (III) above, after step (a).

During the condensation reaction (a) in which ($n+1$) moles of glycerol epihalohydrin are reacted on one mole of alcohol or alkyl phenol, the number of moles of glycerol epihalohydrin fixed by one mole of alcohol or alkyl phenyl to form the recurring units, —[$C_2H_3(CH_2X)O$]—, can be greater or smaller than the value of n and a mixture of compounds, all responding to the general formula III are formed, but in which the number of recurring units varies and all those different numbers are distributed statistically around a mean value represented by $n$. Consequently, n in the final product represents the mean value or the average statistical value of the number of recurring units, —[$C_2H_3(CH_2OH)O$]—, fixed on the different compounds having the general formula I or II.

An important fact which should be emphasized and which constitutes one of the essential advantages of the process of preparing the surface-active agents of this invention is that the present process results in the formation of compounds having a single lipophilic chain per hydrophilic chain.

Moreover, the process of the present invention permits the regulation of the hydrophilic and lipophilic properties of the final product. The hydrophilic characteristic of the resulting surface active agents can be regulated by choosing the value of the number $n$ of moles of glycerol epihalohydrin to be reacted with one mole of fatty alcohol or alkyl phenol. The lipophilic characteristic of the resulting surface active agents can be regulated by choosing the length of the hydrocarbon chain R in the fatty alcohol or alkyl phenol used as an initial reactant.

The following is a detailed description of a preferred embodiment of producing the above surface-active agents.

In step (a), the condensation of glycerol epichlorohydrin or glycerol epibromohydrin on the fatty alcohol or alkyl phenol is carried out in the presence of an acid catalyst, such as boron trifluoride, stannic chloride or antimony pentachloride, at a temperature between 25°–160° C. Preferably boron trifluoride is employed at a temperature between 60°–120° C. The proportion of $BF_3$ with respect to the total mass of reactants ranges between 0.1-0.2 weight percent.

In step (b), the polyhalogenated polyethers, represented by formula (III) above, which result from step (a), are converted to glycidyl ethers (Formula IV) by dehydrohalogenation of the halohydrin, using an aqueous solution of an alkali or alkaline earth metal hydroxide, having a concentration, by weight, of from 20-50 percent. The molar ratio of alkali or alkaline earth metal hydroxide to polyhalogenated polyether ranges between 1:1 to 1:2 and preferably between 1:1.2 to 1:1.5. During this phase of the overall process, which ordinarily is initially conducted at about 20° C or ambient temperature, the reaction temperature rises to about 100° C. When the exothermicity of the reaction ceases, the reaction is terminated by heating the reaction mixture in a water bath. This dehydrohalogenation operation is generally conducted in the presence of a solvent to obtain high reaction speeds and high epoxidation yields. The solvent employed should, preferably, not be miscible with concentrated aqueous solutions of electrolytes so that the resulting polyhalogenated glycidyl ethers can be separated from the reaction medium simply by decantation. Tertiary butyl alcohol and 2-butoxy ethanol are particularly useful solvents when used in weight proportions essentially equal to that of the halohydrin to be dehydrohalogenated. Quaternary ammonium salts comprising a lipophilic chain can be used to improve the contact between the reactants. The resulting polyhalogenated glycidyl ether, if desired, can be isolated by evaporation of the solvent or it can be used in solution in the subsequent stage, i.e., step (c).

In step (c), the polyhalogenated glycidyl ethers from step (b) are reacted with a secondary amine at a temperature from 25°–120° C to open the epoxide ring and thereby form the polyhalogenated tertiary amines having formula (IV).

Alternatively, the polyhalogenated tertiary amines of formula (IV) can be prepared in a single step by reacting the polyhalogenated polyethers from step (a) with a secondary amine in the presence of an alkali or alkaline earth metal hydroxide.

Representative secondary amines usefully employed in the present invention include diethylamine, dipropylamine, morpholine, piperidine and alkanolamines such as diethanolamine, diisopropanolamine/diglycerylamine and N-ethylethanolamine.

The molar ratio of secondary amine to polyhalogenated glycidyl ether in step (c) or the ratio of secondary amine to polyhalogenated polyether (when the alternate route is practiced) to produce polyhalogenated tertiary amines is between about 1:1 to 1:1.5 and, preferably, about 1:1.2.

In step (d), the replacement of the halogen by a hydroxyl in the polyhalogenated tertiary amine from step (c), or from its alternate route, yields the polyhydroxylated amines of the present invention which are useful surface active agents and which are represented by formula I. This operation is carried out with an alkaline salt of a carboxylic acid, such as sodium or potassium acetate, at a temperature between 150°–200° C, preferably about 180° C, in the presence or absence of a solvent.

The presence of a solvent in the reaction medium during step (d) assures both instantaneous and progressive contact among the reactants and easy separation therefrom of the mineral halide formed. Suitable solvents include ethylene glycol, diethylene glycol, propylene glycol, dipropylene glycol as well as the monoalkylethers of these diols such as, monobutyl ether of ethylene glycol and monobutyl ether of diethylene glycol. The hydroxylated solvents also intervene by alcoholysis of the esters formed in an intermediate step.

When the reaction is carried out in the absence of a solvent, as may be the case when the alkaline salt of carboxylic acid is somewhat soluble in the reaction medium, the polyhydroxylated tertiary amine is obtained by alcoholysis of the esters of carboxylic acid with a lower alcohol such as methanol or ethanol, or by saponification followed by salting out or extraction.

In one preferred commercial exploitation of the present invention, the polyhalogenated polyethers from step (a) are reacted with a secondary amine, as defined above, in the presence of an alkali or alkaline earth metal hydrooxide, without isolating the glycidyl ethers thus formed. After reaction with an alkaline salt of carboxylic acid, the esterified amino ethers are separated from the mineral halide by filtration or washing, and then the salts of carboxylic acid are regenerated in situ from the carboxylic esters by saponification with an alkaline hydroxide. Thus, the alkaline salt of carboxylic acid is recovered in aqueous solution and can be used for another hydroxylation reaction.

As stated above, the surface-active agents of this embodiment of the present invention also include the quaternary ammonium salts of the compounds represented by formula I, the quaternary ammonium salts being represented by formula II. To produce said quaternary ammonium salts, the compounds represented by formula I can be reacted with, for instance a quaternizing agent such as methyl sulfate, ethyl sulfate, ethyl chloride, ethyl bromide, methyl iodide, methyl paratoluylene sulfate or methyl methane sulfonate. The mole ratio of quaternizing agent to the compounds represented by formula I corresponds to the stoichiometric amount or is slightly inferior and the reaction is carried out at a temperature ranging from about 15° to 100° C at atmospheric pressure.

Compared, for example, with fatty amines, the surface active agents of the present invention are significantly more water soluble especially at about neutral pH and they lack the odor characteristic of fatty amines and derivatives thereof.

Additionally, the process of the present invention yields stable surface-active agents which are soluble in water over a very wide pH range. The present process also provides surface-active agents which are soluble in concentrated sodium hydroxide without risk of instability which occurs, for example, with the quaternary ammonium hydroxides. Moreover, this result is obtained without the introduction of supplementary ionic groups, and especially anionic groups, which impair the substantive characteristics of the surface-active agents. The solubility characteristics of the surface-active agents of this invention are, of course, highly variable as a function of the values of $n$, R, $R_1$, and $R_2$. Certain of these agents in which R represents alkyl or alkaryl and in which n is equal to 5-6 are soluble in sodium hydroxide. The extent to which these surface-active agents may irritate the skin and mucous membranes is also dependent on the values of $n$, R, $R_1$ and $R_2$. In general, however, the surface-active agents of this invention are clearly less irritating than fatty amines and their derivatives.

The surface active agents of the present invention also provide advantages not secured by such prior art compounds as those disclosed in Luxembourg application No. 48,458 filed Apr. 23, 1965 which are nonionic surface-active agents having the formula

In contradistinction, the surface-active agents of the present invention contain a hydroxy amino propane group

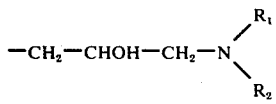

which imparts thereto their cationic characteristics and their substantivity, i.e., their affinity for fibers and particularly for animal and vegetable fibers.

The surface-active agents of the present invention also compare favorably with amino polyethers having the formula

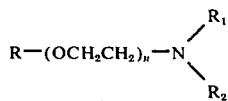

and the substitution of a $-[C_2H_3(CH_2OH)O]-$ group for the oxyethylene group $-(OCH_2CH_2)-$ is very useful.

The surface-active agents of this embodiment of the present invention because of their physical and chemical characteristics are suitably employed in cosmetic preparations, and particularly in shampoo, hair dyes, hair rinses and permanent waving compositions. Further when the surface-active agents of this embodiment of the present invention, are used in compositions for treating hair, they impart to the hair a certain sheen and a pleasing texture. The hair is particularly soft, odorless and is easily untangled.

Thus, in accordance with the present invention there is provided a shampoo composition comprising an aqueous solution of the surface-active agents of this invention present in amounts of about 0.5 to 10 percent by weight of said shampoo composition, having a pH ranging from about 3 to 6.5. The pH can be adjusted to the desired value by incorporating into said composition an acidic component such as an organic acid including lactic, acetic or citric acid and the like.

In another embodiment of the present invention hair is permanently waved by applying to the hair wound on curlers during the first stage, i.e., during the reducing stage, a composition comprising a reducing agent, permitting the composition to remain on the hair for a time sufficient to alter the disulphide bonds of the keratin of the hair, generally about 10–40 minutes, thoroughly rinsing the hair to remove residual reducing agent and applying in the second stage, i.e., during the neutralization state, a cosmetic composition comprising a mixture of an oxidizing or neutralizing agent and the surface-active agent of the present invention, whereby the disulphide bonds of the keratin of the hair are reformed.

Conventional reducing agents employed are advantageously those organic thiols which are generally used to perform the first stage of a permanent waving operation. Representative thiols include thioglycolic acid and its salts, glycol thioglycolate, glycerol thioglycolate, thioglycolic amide, thiolactic acid, glycol thiolactate, β-mercaptoethanol, N-carboxymethyl mercapto acetamide, β-mercapto propionic acid and the like. Generally the composition comprising the reducing agent is an aqueous solution of said reducing agent present in amounts of about 2 to 15 percent by weight thereof and having a pH ranging from about 8 to 10.

The neutralizing composition of the present invention comprises an aqueous solution of 0.5 to 4 weight percent of a conventional neutralizing or oxidizing agent and about 0.2 to 5 weight percent of the surface active agent of this invention. Conventional neutralizing agents employed include, for instance, hydrogen peroxide, sodium or potassium bromate, sodium perborate or percarbonate and the like.

The surface-active agents of the present invention are also usefully employed in hair dye compositions comprising a solution in a solvent selected from the group consisting of water, an aqueous solution of a lower alkanol such as ethanol and isopropanol of a glycol such as butyl glycol, propylene glycol, ethylene glycol, 3-amyloxy 4-propane 1,2-diol, and of ethers of glycol such as monobutyl ether of ethylene glycol wherein said alkanol and/or glycol and/or ether of glycol is present in amounts of about 8 to 25 percent by weight of said solution, a hair dye such as azo, anthraquinone and nitro dyes of the benzene series, and 0.5 to 6 percent by weight of the surface-active agent of the present invention.

Additionally, if desired, said hair dye composition can include its weight of 6% hydrogen peroxide to provide said composition in gel form.

Generally the dye is present in amounts of about 0.1 to 5 percent by weight of said composition which has a pH ranging from about 8 to 10.5.

Representative dyes include paraphenylene diamine, 2,5-toluene diamine sulfate, chloroparaphenylene diamine sulfate, nitroparaphenylene diamine, 1,2,4-triaminobenzene trihydrochloride, paraaminodiphenyl amine, ortho phenylene diamine, 4-chloro ortho phenylene diamine, 4-nitro ortho phenylene diamine, paraaminophenol, 4-amino 2-methyl phenol slfate, 4-amino-3-methyl phenol, 4-amino 2-nitro phenol, m-diamino anisol and its sulfate, p-aminophenol and its sulfate, nitro-p-phenylene diamine, p-toluylene diamine, resorcine, hydroquinone, 3-nitro 4-β-aminoethylamino anisole hydrochloride, 2-4-diaminophenol hydrochloride, paramethyl aminophenol sulfate, ortho aminophenol, 4-cloro 2-aminophenol, 4-nitro 2-aminophenol, 5-nitro 2-aminophenol, 4,6-dinitro 2-aminophenol, 6-chloro 4-nitro 2-aminophenol hydrochloride, 4-amino diphenylamine, 4,4'-diamino diphenylamine sulfate, metaphenylene diamine, chloro-meta phenylene diamine, nitro-meta phenylene diamine, meta tolulylene diamine, 2,4-diamino anisol sulfate, meta aminophenol, 3,5-diaminophenol hydrochloride, diethyl meta aminophenol, paraamino ortho cresol, 1-dimethylamino 3-amino ethylamino 4-nitro benzene, 1-hydroxy-2,4-di(p-trimethylammoniumphenylamino) anthraquinone methosulfate, 1-hydroxy-2,4-di (p-trimethyl-ammoniumphenylamino) anthraquinone iodide, 1-amino propylamino anthraquinone.

1,8-Bis-γ-aminopropylamino anthraquinone, 1-diethylamino 2-ethylamino-nitro-4-NN-dihydroxyethylamino benzene dihydrochloride, 4-N-methylamino-3-nitro-1-N-β-aminoethylamino benzene, [l-hydroxy-4-(γ methylmorpholinium) propylamino anthraquinone ]methyl sulfate, 2-β-aminoethylaminoanthraquinone, 1,5-di-(β-aminopropylamino) anthraquinone, 1-methylamino-4-amino propylamino anthraquinone, 1-amino propylamno-anthraquinone 1,4-diamino-5-γ aminopropylamine-anthraquinene. Additional examples of commercially available useful dyes include, as monoazo dyes, Cl Acid Blue 92 (1339 ) ) and CI Acid Yellow 23 (19140); as diazo dyes, Cl Acid Orange 24 (20170); as triphenylmethane type dyes, Cl Acid Blue 1 (42045), Cl Acid Violet 19 (42685), Cl Acid Blue 22 (42755) and Cl Acid Violet 15 (43525); as xanthene dyes, Cl Acid Violet 9 (45190); as azine dyes, Cl Acid Black 2 (50420), Cl Acid Blue 59 (50315) and Cl Acid Blue 61 (50330); as anthraquinone dyes, Cl Acid Violet 43 (60730), Cl Acid Blue 80 (61585), Cl Acid Violet 51 (62165) and Cl Acid Blue 138 (62075); as premetallized dyes, both 1:1 and 2:1 complexes, chromium and cobalt, for instance Cl Disperse Blue 14 (61500), Cl Disperse Blue 6 (62050) and Cl Disperse Blue 31 (64505); as direct dyes, Cl Direct Blue 2 (22590), Cl Direct Black 51 (27720) and Cl Direct Violet 51 (27905); and as solvent dyes, (15680) and Cl Solvent Violet 10 ; (45190).

The surface-active agents of the present invention are also usefully used in hair rinses. These hair rinses are employed on the hair in order to make easier its disentanglement, especially when same is electric or curly. These hair rinses comprise a solution in a solvent selected from the group consisting of water and an aqueous solution of a lower alkanol such as ethanol and isopropanol wherein said alkanol is present in amounts of about 15 to 60% by weight of said solution, a cosmetic resin in amounts of about 0.5 to 5% and 0.1 to 2% by weight of surface-active agents of the present invention. This composition may also comprise a perfume in amounts of about 0.05 to 0.5% and hair dyes from an amount of about 0.005 to 3% of said composition which has a pH from about 7 to 8.5. Representative cosmetic resins include polymers, i.e. polyvinyl pyrrelidone (PVP) having a molecular weight ranging between 40,000 to 360,000 the preferred molecular weight being 40,000, or copolymers such as the copolymer of vinyl pyrrolidone and vinyl acetate (MW = 40,000 - 160,000) 70% : 30% to 30% : 70%, the preferred proportion being 60% : 40% having a viscosity of 3.3 to 4 centipoises in 5% solution in ethanol; or copolymers of crotonic acid and vinyl acetate 90% : 10% having a molecular weight of 40,000 to 200,000 and preferably of 50,000 and a viscosity of 7 to 9 centipoises in 5% solution in tetrachlorethane; or monoalkyl ester of the copolymer of methylvinyl ether and maleic acid.

Representative hair dyes include direct dyes such as azo dyes, triphenylmethane type dyes, xanthene dyes, anthraquinone dyes, azine dyes, premetallized dyes, solvent dyes and the like. All the above cited dyes are commercially available useful dyes may be used.

In use, the compounds of the present invention can be in the form of salts of inorganic and organic acids such as hydrochloric, phosphoric, boric, acetic, citric and lactic acids.

II. Preparation of Surface-Active Agents Which Are The Condensation Products Of An Alcohol And Glycerol Epihalohydrin

EXAMPLE 1

185 g of glycerol epichlorhydrin are reacted with one mole, i.e., 186 g of dodecanol at 75–80° C in the presence of 1.5 ml of an acetic acid complex containing 36% BF$_3$. Dodecyl ether of polyepichlorhydrin having the following formula is obtained:

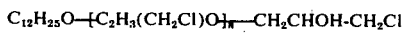

in which $n$ has a statistical average value of 1.

371 g of this compound are dissolved in an equal weight of tertiary butyl alcohol and 148 g of an aqueous 40% solution of sodium hydroxide are added drop by drop, while stirring.

The temperature rises from 25° to 28° C.

The mixture is then heated to from 65°–70° C while stirring.

After being cooled to ambient temperature, the sodium chloride precipitate is dissolved by adding 300 cm$^3$ of water.

The aqueous phase containing the sodium chloride and the excess sodium hydroxide is drawn off.

The organic phase is left overnight, then filtered.

After evaporation of the tertiary butyl alcohol first under normal pressure, then under the vacuum of a water-jet pump, the glycidyl ether having the following formula is collected:

with a 98% yield.

The resultant product has an epoxide content equal to 97% of the theoretical value.

160.5 g are added to 69 g of 97% pure diisopropanolamine.

The mixture is heated to 95° C for 3 ½ hours and the tertiary amine having the following formula is obtained with a 94% yield:

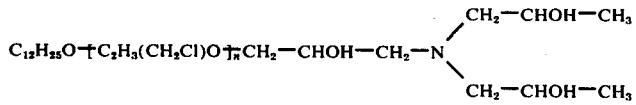

In this formula $n$ has a statistical average value of 1. This compound is water soluble in an acid medium.

222 g of this chlorinated amine are then heated with 46.6g of potassium acetate in the presence of 260 g of dipropylene glycol at 180°–185° C for 3 hours.

The potassium chloride is separated by filtration, then the dipropylene glycol is evapoarated in a vacuum.

In order to complete the de-acetylation, 166 g of the product are dissolved in 200 g of absolute ethyl alcohol. 1 cm$^3$ of a 25% solution of sodium methylate in methanol is added and the mixture is left at ambient temperature for 18 hours.

The ethyl acetate formed and the alcohol, are evaporated, and 163.5 g of the compound having the following formula are collected:

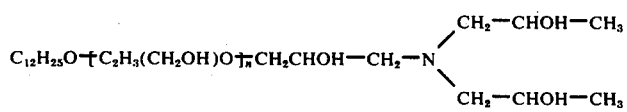

Here $n$ has a statistical average value of 1.

This product is in the form of a colorless viscous oil, soluble in water, with a pH less than or equal to 7, this pH being adjusted by adding lactic acid.

EXAMPLE 2

The process is the same as in Example 1, except that the diisopropanolamine is replaced by diethanolamine. The polychlorinated tertiary amine having the following formula is prepared:

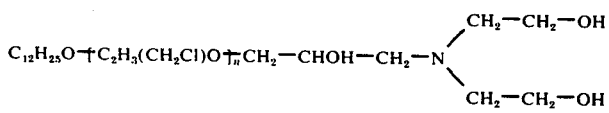

$n$ having a statistical average value of 1 with a yield of about 93%.

After treatment with potassium acetate at 180°–185° C in dipropylene glycol, filtration, evaoration of the dipropylene glycol and ethanolysis, the compound having the following formula is obtained:

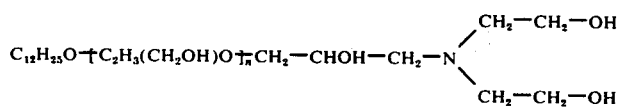

$n$ has a statistical average value of 1.

This compound takes the form of a viscous yellow oil, soluble in water and having a pH less than or equal to 7.5. It forms gels at a 4% concentration at a pH of 7.5 to 7.2 in an aqueous medium (the Ph being adjusted with lactic acid).

EXAMPLE 3

4.5 moles of glycerol epichlorohydrin are reacted with 3 moles of a mixture of fatty alcohols containing about 55% dodecanol and 43.5% tetradecanol. The product is monoalkyl ether of polyepichlorohydrin having the formula:

RO─[ C₂H₃O(CH₂Cl) ─]ₙ CH₂─CHOH─CH₂Cl in which $n$ has a statistical average value of 0.5 and R represents an alkyl radical with 12 to 14 carbon atoms.

This compound is then dehydrohalogenated according to the process described in Example 1.

Glycidyl ether having the following formula is obtained:

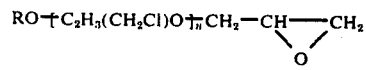

in which R and $n$ have the meaning given above.

On being heated at 90°–95° C for 2 hours, this product reacts with the diisopropanolamine at a 5% molar excess to form the tertiary amine:

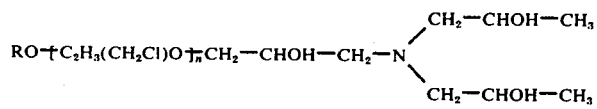

with a 94% yield.

Then, after treatment with potassium acetate at 180°–185° C, dipropylene glycol being used as the solvent, filtration of the potassium chloride and evaporation of the solvent, the polyhydroxyl amine having the following formula is obtained:

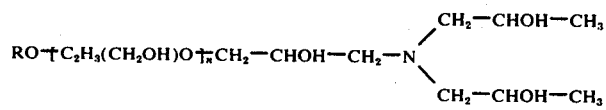

with $n$ and R having the meaning given above.

EXAMPLE 4

The process is the same as in Example 3, except that the diisopropanolamine is replaced by diethanolamine in identical molar proportions. The chlorinated amine having the following formula is prepared:

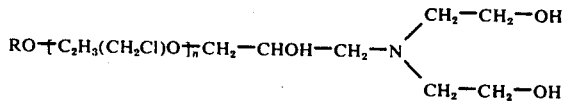

R is alkyl having 12–14 carbon atoms, $n$ has a statistical average value of 0.5.

By hydroxylation at 180°–185° C for 3 hours in dipropylene glycol, with a stoichiometric quantity of potassium acetate with respect to the chlorine, the polyhydroxyl amine having the following formula is obtained:

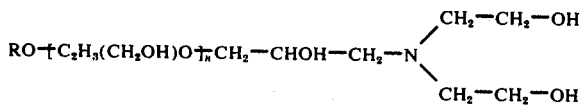

in this formula R and $n$ have the meaning given above.

EXAMPLE 5

By condensation of 2 moles of glycerol epichlorohydrin on one mole of a mixture of fatty alcohols identical to that used in Examples 3 and 4, the monoether of polyepichlorohydrin having the following formula is first prepared:

RO─[C$_2$H$_3$(CH$_2$Cl)O]$_n$CH$_2$ CHOH CH$_2$Cl in which R represents an alkyl having 12 to 14 carbon atoms and $n$ has a statistical average value of 1.

This product is then dissolved in tertiary butyl alcohol and dehydrohalogenated with an aqueous 40% solution of sodium hydroxide in an excess of 50% with respect to the quantity theoretically necessary.

After decantation of the organic phase, drying on sodium sulfate, and evaporation of the tertiary butyl alcohol, glycidyl ether having the following formula is obtained:

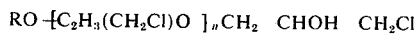

In this formula R and $n$ have the same meaning as above. Yield: 98.5%. Epoxide content: 100% of the theoretical value.

This product, when reacted at 95° C with diethanolamine in a molar excess of 5% yields the chlorinated amine having the following formula:

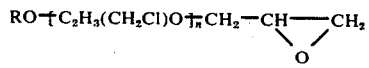

again R and $n$ have the meaning given above. Yield: 98%.

Potassium acetate at a molar excess of 10% is then substituted for the chlorine at 180°–185° C, using a quantity of dipropylene glycol equal in weight to that of the chlorinated aime as the solvent.

The potassium chloride is removed by filtration and the solvent is evaporated in a vacuum.

The raw product, in which about 7% of the alcohol functions are esterified by acetic acid, is purified in the following manner:

The esters are saponified with an aqueous 14% solution of sodium hydroxide in stoichiometric proportions.

The hydroxyl aime is dissolved in an equivalent weight of butyl monoether of diethylene glycol. The organic phase is washed twice with boiling water, and the liquid is decanted while hot.

After removal of the water and solvent, a compound having the following formula is obtained:

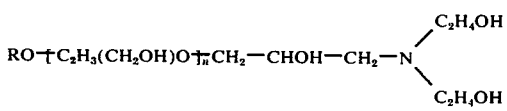

wherein R and $n$ have the meaning given above.

This product is a yellow-orange oil which is soluble in water at a pH of 7 (the pH being adjusted by the addition of lactic acid).

EXAMPLE 6

By using the same glycidyl ether as in Example 5, but replacing the diethanolamine with morpholine in the same molar proportions, the chlorinated amine having the following formula is obtained:

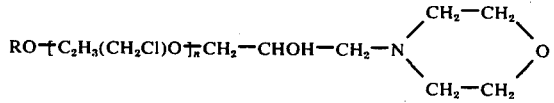

in this formula R represents an alkyl radical with 12 to 14 carbon atoms and $n$ has a statistical average value of 1.

This product is then dissolved in an equivalent weight of monobutylether of diethylene glycol and heated to 180°–185° C for 4 hours with a 10% excess of potassium acetate.

After the potassium chloride has been separated by filtration, the acetic esters are saponified with aqueous soda in a stoichiometric quantity. A weight of water equal to that of the filtrate is added and the mixture is heated to 70° C. It separates into two phases.

The aqueous phase, containing the sodium acetate, is drawn off while hot.

The water and solvent are evaporated together from the organic phase by progressive elevation of the temperature to 180° C under a pressure of 18 mm of mercury.

An orange oil is obtained.

This product has the following formula:

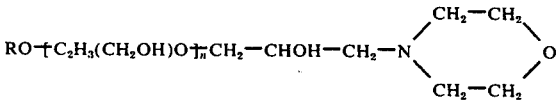

in which R represents alkyl having 12 to 14 carbon atoms and $n$ has a statistical average value of 1. The product is soluble in water which has been acidified with lactic acid to pH 6.3.

EXAMPLE 7

2 moles of epichlorohydrin are reacted with one mole of industrial oleyl alcohol. The monoether of polyepichlorohydrin having the following formula is obtained:

RO —[ C₂H₃(CH₂Cl)O ]ₙ CH₂—CHOH—CHOH—CH₂Cl

In this formula R represents the 9-octadecenyl radical, $n$ having a statistical average value of 1.

After treatment with an aqueous solution containing 40% sodium hydroxide at an excess of 50% in the presence of tertiary butyl alcohol, this yields the corresponding glycidyl ether. Yield: 98%. Expoxide content: 98% of the theoretical value.

The tertiary chlorinated amine having the following formula

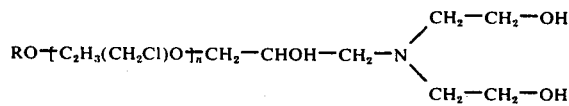

with R and $n$ having the meaing given above, is prepared by heating this epoxide with diethanolamine at a 5% molar excess, the temperature being held at 95° C for 2 hours.

Hydroxylation is then carried out as described above, with potassium acetate and dipropylene glycol.

After filtration of the salt and evaporation of the solvent, the resultant product may be purified as follows:

200 g of the product are dissolved in 200 g of monobutylether of diethylene glycol.

The acidic esters are saponified by addition of a stoichiometric quantity of an aqueous solution containing 40% sodium hydroxide. Then 200 g of hot water are added, the mixture is stirred for several minutes, and the aqueous phase containing the sodium acetate is drawn off.

After evaporation of the water and solvent, 195 g of the product having the following formula are collected:

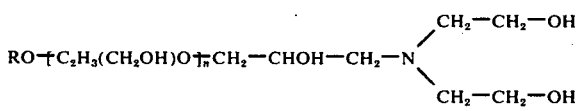

This compound is soluble in water at a pH of about 6.5, this pH being adjusted with lactic acid.

EXAMPLE 8

From the oleyl alcohol identical to that used in Example 7, the following compounds are successively prepared. First, the oleyl ether of polyepichlorohydrin having the formula:

RO—[C₂H₃(CH₂Cl)O]ₙ CH₂-CHOH-CH₂-Cl in which:
 R = 9-octadecenyl(oleyl), and
 $n$ has a statistical average value of 3, and then the corresponding glycidyl ether having the formula:

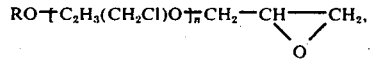

wherein R and $n$ have the meaning given above.

By opening the epoxide with diethanolamine under the same conditions as before, the following chlorinated amine is obtained:

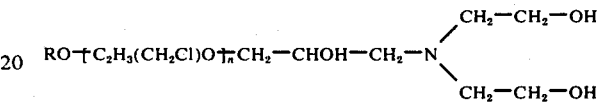

wherein R and $n$ have the meaning given above.

This product is then dissolved in an equivalent weight of monobutylether of diethylene glycol and heated to 180°–185° C for 3 hours with potassium acetate.

1.10 mols of potassium acetate are used per gramatom of chlorine.

The percent transformed, calculated on the basis of the consumption of the acetate, is about 98%.

The potassium chloride is separated by filtration. The solvent is then evaporated in a vacuum by progressively raising the temperature to 180° C.

The raw product is dissolved in alcohol, decolorized with animal charcoal, then ethanolyzed with sodium methylate as a catalyst.

0.5 g of catalyst is used per 100 g of the product.

The alcohol and ethyl acetate which has formed are evaporated.

The polyhydroxylated amine having the following formula is obtained:

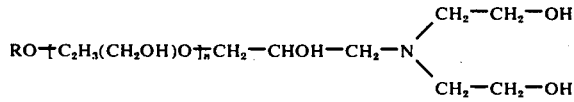

R = 9-octadecenyl and
$n$ has a statistical average value of 3.

This is a very viscous oil which is soluble in water at 25° C. The pH of a M/10 solution is about 9.3.

EXAMPLE 9

After reacting 264 g of "Hexadecylic" alcohol (sold commercially the Esso Corporation) with 185 g of epichlorohydrin at 60° C in the presence of 1.2 ml of an acetic acid complex of boron fluoride, a polychlorinated polyether having the following formula is obtained:

$$\begin{array}{c} C_6H_{13} \\ \phantom{C_6H_{13}}\diagdown \\ \phantom{CCCCC}CH-CH_2O+C_2H_3(CH_2Cl)O\overline{)_n}CH_2-CHOH-C_2Cl, \\ \phantom{C_6H_{13}}\diagup \\ C_8H_{17} \end{array}$$

$n$ has a statistical average value of 1.

In 200 g of monobutylether of diethylene glycol at ambient temperature, the following are successively dissolved:

179.6 g of polychlorinated polyether and
46 g of diethanolamine at 96%.

Then, drop by drop, 44 g of an aqueous 40% solution of sodium hydroxide are added. The temperature of the reaction mixture rises to 32°.

The mixture is stirred for 15 minutes first, at ambient temperature and then in a boiling water-bath for one hour.

A polychlorinated amine having the following formula is thus obtained:

$$\begin{array}{c} C_6H_{13} \\ \phantom{C_6H_{13}}\diagdown \\ \phantom{CCCCC}CH-CH_2O+C_2H_3(CH_2Cl)O\overline{)_n}CH_2-CHOH-CH_2-N \\ \phantom{C_6H_{13}}\diagup \\ C_8H_{17} \end{array} \begin{array}{c} \diagup CH_2-CH_2-OH \\ \diagdown CH_2-CH_2OH \end{array}$$

wherein $n$ has a statistical average value of 1.

This product is soluble in water in an acid medium.

The hydroxylation reaction is carried out as follows:

The excess sodium hydroxide is neutralized with 2.4 g of pure acetic acid. Then 31.8 g of anhydrous sodium acetate are added.

The mixture is heated to 185°–190° C for 6 hours after the water has been removed by evaporation.

The sodium chloride is separated by filtration; then the acetic esters formed are saponified with 37.6 g of a 40% solution of sodium hydroxide.

After addition of 650 g of water, the mixture is heated to 90° C.

When allowed to settle, the mixture separates into two phases. The aqueous phase containing the electrolytes is drawn off, then the solvent of the organic phase is evaporated.

180 g of the product having the following formula are obtained:

$$\begin{array}{c} C_6H_{13} \\ \phantom{C_6H_{13}}\diagdown \\ \phantom{CCCCC}CH-CH_2-O+C_2H_3(CH_2OH)O\overline{)_n}CH_2CHOH-CH_2-N \\ \phantom{C_6H_{13}}\diagup \\ C_8H_{17} \end{array} \begin{array}{c} \diagup CH_2-CH_2-OH \\ \diagdown CH_2-CH_2-OH \end{array}$$

wherein $n$ has a statistical average value of 1.

This compound is a clear yellow oil and is soluble in water at a pH of 3.

The tertiary amines prepared in the preceding Examples may be transformed into quaternary ammonium salts. This may be done very easily, particularly by using metyl sulfate, as shown in the following example:

EXAMPLE 10

To 50 g of a polyhydroxylated tertiary amine having the following formula:

$$RO+C_2H_3(CH_2OH)O\overline{)_n}CH_2-CHOH-CH_2-N\begin{array}{c} \diagup CH_2-CH_2-OH \\ \diagdown CH_2-CH_2-OH \end{array}$$

wherein R represents an alkyl radical having 12 to 14 carbon atoms and $n$ has a statistical average value of 0.5, 14.7 g of methyl sulfate are added, drop by drop, at 40° C. The temperature of the mixture rises to 70° C.

The addition of the methyl sulfate takes about 15 minutes. The reaction is terminated by heating in a boiling water bath.

The product is a water-soluble paste and has the following formula:

$$RO+C_2H_3(CH_2OH)O\overline{)_n}CH_2-CHOH-CH_2-\overset{+}{\underset{|}{N}}\begin{array}{c} \diagup CH_2-CH_2-OH \\ \diagdown \end{array} \cdot SO_4CH_3^-$$
$$\phantom{RO+C_2H_3(CH_2OH)O_nCH_2-CHOH-CH_2-N}CH_3CH_2-CH_2-OH$$

wherein R and $n$ have the meaning given above.

Example 10 is repeated using, instead of methyl sulfate, essentially comparable amounts of ethyl chloride, ethyl bromide, methyl iodide, methyl paratoluylene sulfate and methyl methane sulfonate to obtain similar quaternary ammonium salts.

EXAMPLE 11

The monoether of polyepichlorohydrin, having the following formula, is prepared by condensing 2 moles of glycerol epichlorohydrin on a molar equivalent quantity of a mixture of fatty alcohols identical to that used in Examples 3, 4 and 5:

$$RO+C_2H_3(CH_2Cl)O\overline{)_n}CH_2\text{-}CHOH\text{-}CH_2Cl$$

In this formula:

R represents alkyl having 12 to 14 carbon atoms, and $n$ has a statistical average value of 1.

40.5 g of anhydrous diethylamine are added to 191 g of this product. Then 55.5 g of an aqueous 40% solution of sodium hydroxide are added to the mixture in 5 minutes with stirring. The temperature rises from 25° to 31° C. The reaction mixture is progressively heated to 90° C in 35 minutes and is kept at this temperature for one hour.

After the electrolytes have been dissolved in 76 g of water, a chlorinated amine having the following formula is separated by salting out at 90° C:

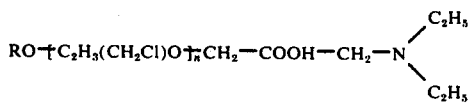

wherein R and *n* have the meaning given above.

After dehydration the product is 93% pure according to amino group determinations. The chlorine is substituted using potassium acetate in dipropylene glycol at 180° C.

This process takes three hours. The raw product collected after filtration and evaporation of the solvent is deacetylated by saponification with sodium hydroxide and washed with an equivalent weight of water at 80°-85° C. After decantation and dehydration in a vacuum, a yellow-orange oil having the following formula is obtained.

$RO\text{--}[C_2H_3(CH_2OH)O]_{\overline{n}}CH_2\text{--}CHOH\text{--}CH_2\text{--}N\begin{smallmatrix}C_2H_5\\C_2H_5\end{smallmatrix}$ wherein R and *n* have the meaning given above.

This compound is soluble in water at a pH less than or equal to 6 (the pH being adjusted with lactic acid).

EXAMPLE 12

As in Example 7, a monoether of polyepichlorohydrin having the following formula is first prepared:

$RO\text{--}[C_2H_3(CH_2Cl)O]_nCH_2\text{--}CHOH\text{--}CH_2Cl$

In this formula:
R represents an 9-octadecenyl and
*n* has a statistical average value of 1.

This product is then condensed with morpholine at 95° C in the presence of sodium hydroxide. The process takes 1½ hours. The molar proportions of sodium hydroxide to chlorohydrin and amine to chlorohydrin are 1.05:1.

After neutralization of the excess sodium hydroxide with acetic acid, a chlorinated amine having the following formula is obtained:

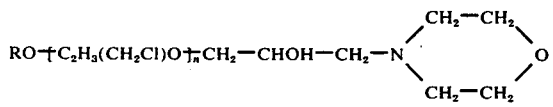

wherein R and *n* have the meaning given above. This product is mixed with an equivalent weight of diethylene glycol and reacted with sodium acetate at 180°-185° C for 3½ hours. This reactant is added as an aqueous solution, the water being removed from the reaction medium by evaporation. 1.05 moles of acetate are used per atom of chlorine to be replaced.

After removal of the salt by filtration and evaporation of the solvent, the product is a brown oil. It is soluble in water at a pH less than or equal to 4.5 (the pH being adjusted with lactic acid). It has the following formula:

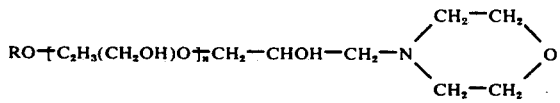

wherein R and *n* have the meaning given above.

EXAMPLE 13

By the same process as in Example 12, except that morpholine is replaced by diisopropanolamine, a compound having the following formula is prepared:

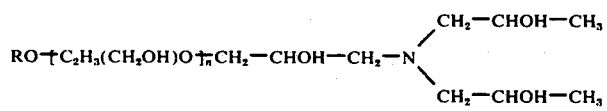

In this formula:
R represents 9-octadecenyl and
*n* has a statistical average value of 1.

This product is soluble in water at a pH less than or equal to 5.5 (the pH being adjusted with lactic acid).

EXAMPLE 14

The procedure is the same as in Example 12, except that instead of using oleyl alcohol having an 85% purity (as in Examples 7, 12 and 13), the first step is to prepare from an oleyl-cetyl alcohol sold under the trademark "Ocenol HD-50-55" by the Dehydag Company, which is a commercial "oleyl-cetyl" alcohol, having an iodine index of 45-55, a chlorinated amine having the formula:

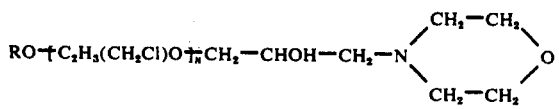

wherein R represents a hydrocarbon radical having 12 to 18 carbon atoms, and

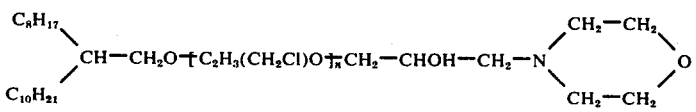

$n$ has a statistical average value of 1.

The chlorine is then substituted using potassium acetate in dipropylene glycol as a solvent.

Reaction temperature: 180°–185° C
Duration: 5½ hours.

The product obtained after filtration and evaporation of the solvent has the following formula:

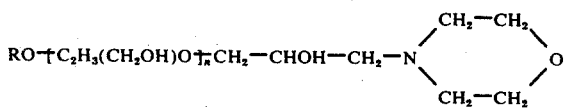

wherein R and $n$ have the meaning given above.

Ocular tests on rabbits have shown it to be absolutely harmless when applied as an aqueous solution having a pH of 4 and an active product concentration of one-tenth mole/liter.

EXAMPLE 15

The monoether of polyepichlorohydrin having the following formula is prepared by reacting two moles of epichlorohydrin with a molar equivalent quantity of 2-octyldodecanol (sold under the trademark "EUTANOL-G") in the presence of 1.2 ml of an acetic acid complex of boron fluoride:

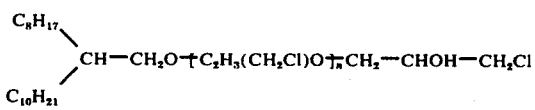

wherein $n$ has a statistical average value of 1.

This compound is then condensed with morpholine in the presence of sodium hydroxide.

Molar proportion of morpholine: chlorohydrin = 1.05
Molar proportion of sodium hydroxide: chlorohydrin = 1.10

The mixture is heated to 95° C for 2½ hours.
A chlorinated amine having the following formula:

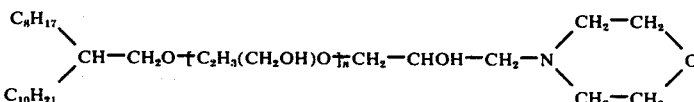

wherein $n$ has the meaning given above and obtained after washing and dehydration, has an amine group content of 1.70 meq/g.

The chlorine is then substituted by heating said amine at 180°–185° C with a 5% excess of anhydrous potassium acetate with respect to the quantity theoretically necessary. Dipropylene glycol is used as the solvent. The process takes four hours.

After filtration and evaporation of the dipropylene glycol, the acetic esters are saponified with an aqueous 40% solution of sodium hydroxide. Then the product is washed with a mixture of equal weights of water and methanol.

A polyhydroxylated amine having the following formula:

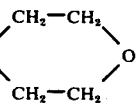

in which $n$ has a mean statistical value of 1, is obtained in the form of a yellow-orange oil.

EXAMPLE 16

The monoether of polyepichlorohydrin, having the following formula, is prepared by reacting 3 moles of glycerol epichlorohydrin with 0.5 mole of nonylphenol in the presence of 0.85 ml of acetic of boron fluoride at 70°–85° C:

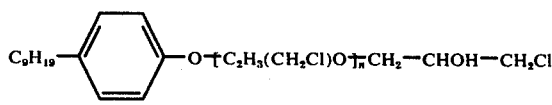

In this formula $n$ has a statistical average value of 5. The theoretical hydroxyl index of this product is 72 (found 85). 150 g of this polychlorinated polyether are treated with 26.6 g of diethanolamine in the presence of 23.9 g of an aqueous 40% solution of sodium hydroxide. 215 g of diethylene glycol are used as a solvent. After 2 hours of heating at 90°–95° C, the percentage of transformation is about 95%.

A polychlorinated teriary amine having the following formula is obtained:

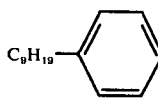 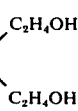

The chlorine is then replaced as follows:
The sodium hydroxide remaining in the reaction mixture is neutralized with acetic acid. The mixture is heated to 180°–185° C and 0.5 mole of aqueous sodium acetate is added in 45 minutes. The water is removed by evaporation.

After an hour of heating at 180°–185° C, 45.1 g of an aqueous 40% solution of sodium hydroxide are added in 1½ hours, and the sodium acetate is thus recovered from the acetic esters previously formed. The temperature is kept at 180°–185° C for 2½ hours after the sodium hydroxide has been added. After cooling, the salt is removed by filtration and the diethylene glycol is evaporated under reduced pressure. A polyhydroxylated amine having the following formula is obtained:

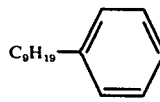 

In this formula $n$ has a statistical average value of 5.
The product is soluble in water at a pH of 9 and in a 10% sodium hydroxide solution.

EXAMPLE 17

By proceeding as in Example 16, except that the diethanolamine is replaced by morpholine, a polyhydroxylated amine having the following formula is prepared:

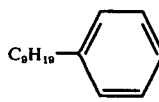 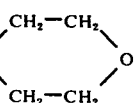

wherein $n$ has a statistical average value of 5.
This compound is soluble in water, the pH of the solution being 9.

Examples 16 and 17 are repeated using, instead of nonylphenol, comparable amounts of octylphenol and dodecylphenol.

EXAMPLE 18

An alcohol having an average molecular weight of 290 is prepared by catalytic reduction, in the manner conventionally used to reduce fatty alcohols, of the isostearic acid sold commercially by the Emery Company.

The isostearic acid used has the following properties:

| | |
|---|---|
| Iodine index | 10 |
| Saponification index | 5.6 |
| Titer | 10° |

By reacting 0.3 mole of alcohol with 0.6 mole of epichlorohydrin in the presence of 0.4 ml of an acetic acid complex of boron fluoride at 70°–75° C, a polychlorinated polyether having the following formula is obtained:

$$RO-[C_2H_3(CH_2Cl)O]_{\overline{n}}CH_2-CHOH-CH_2Cl$$

wherein R represents an alkyl radical derived frm isostearic acid, and $n$ has a mean statistical value of 1.

60 g of the clear yellow oil which results are mixed with 19 g of diisopropanolamine. Then 14.5 g of an aqueous 40% sodium hydroxide solution are added.

After 1½ hours of heating at 95° C, the product is completely soluble in water in an acid medium. From a determination of the tertiary amines, the percentage of transformation is approximately 100%.

The resulting chlorinated amine is now changed to a polyhydroxylated amine as follows:

The following substances are successively added to the reaction mixture:
  0.8 ml of glacial acetic acid,
  120 g of dipropylene glycol, and
  11.45 g of anhydrous potassium acetate.

The mixture is heated to 180°–185° C for 6 hours. After cooling the salt is removed by filtration and the dipropylene glycol is evaporated under reduced pressure.

The resulting product, whose saponification index is 5.6, is treated with 1 g of an aqueous 40% sodium hydroxide solution, then washed at 95° C with 70 g of water. After decantation and drying in a vacuum, a polyhydroxylated amine having the following formula is obtained:

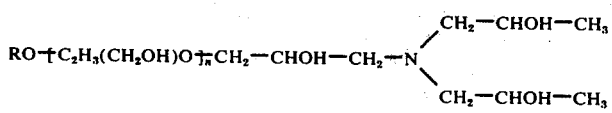

wherein R represents a hydrocarbon radical derived from isostearic acid, and $n$ has a statistical average value of 1.

The compound is a straw-yellow oil.

Examples 19–28 which illustrate the preparation of additional surface active agents in accordance with this embodiment of the present invention are set forth below in Table I.

TABLE I

Step (a)

| Example No. | Alcohol R | (Grams) | Moles | Catalyst BF₃/CH₃COOH (ml) | Glycerol Epichlorohydrin (Grams) | Moles | n+1 | Polyhalogenated Hydroxyl Index Of Resulting Polyether Found | Theoretical |
|---|---|---|---|---|---|---|---|---|---|
| 19 | cetyl/stearyl | 143 | 0.5 | 1.5 | 462.5 | 5 | 10 | 57–58 | |
| 20 | " | 532 | 2.1 | 2.2 | 370 | 4 | 1.9 | 128 | 131 |
| 21 | " | " | " | " | " | " | " | " | " |
| 22 | " | " | " | " | " | " | " | " | " |
| 23 | *residue of | 410 | 2 | 3 | 832 | 9 | 4.5 | 95.5 | 90.5 |
| 23 | *residue of Dobanol | 410 | 2 | 3 | 832 | 9 | 4.5 | 95.5 | 90.5 |
| 24 | Hexadecyl | 132 | 0.5 | 0.8 | 185 | 2 | 4 | 95 | 88 |
| 25 | Nonylphenyl | 220 | 1 | 1 | 185 | " | 2 | 145 | 138 |
| 26 | " | 114.5 | 0.5 | 0.7 | " | " | 4 | 108 | |
| 27 | " | " | " | " | " | " | " | " | |
| 28 | " | 220 | 1 | 1 | 185 | 2 | 2 | 145 | 138 |

*Dobanol (Shell) Mixture of saturated principally straight chained aliphatic alcohols having 11–15 carbon atoms (14% branched chained)

Step (b) / Step (c)

| Example No. | Polyhalogenated Polyether (from Step a) (Grams) | Moles | NaOH (40% soln.) (Grams) | Secondary Amine Nom | (Grams) | % Excess | Time (Hours) |
|---|---|---|---|---|---|---|---|
| 19 | 200 | 0.2* | 22.8 | Piperidine | 23 | 5 | 1.5 |
| 20 | 214.5 | 0.49 | 54 | Morpholine | 44.7 | 5 | " |
| 21 | 200 | 0.45 | 50 | Diethanolamine | 50.8 | 5 | " |
| 22 | " | " | " | Diisopropanolamine | 65.5 | 5 | " |
| 23 | 1200 | 2.09 | 219 | Diethanolamine | 244 | 10 | 2 |
| 24 | 190 | 0.3 | 50 | Morpholine | 27.5 | 5 | 2 |
| 25 | 202 | 0.5 | 55 | Diethanolamine | 57.5 | 5 | 2.5 |
| 26 | 125 | 0.24 | 25.4 | " | 28.2 | 10 | 1.5 |
| 27 | " | " | " | Morpholine** | 23.2 | 10 | 3 |
| 28 | 150 | 0.33 | 36.3 | Morpholine*** | 30.2 | 5 | 1.5 |

200 g dipropylene glycol added as solvent
*180 g dipropylene glycol added as solvent
**150 g tertiobutyl alcohol added as solvent

Step (d)

| No. | Solvent Type | (Grams) | Potassium Acetate (Grams) | CH₃COOH (Grams) | NaOH 40% (Grams) | Time At 185° C. (Hours) | Alcoholysis Absolute Ethyl Alcohol | Saponification NaOH-40% Soln. (Grams) | Salting Out (in water) |
|---|---|---|---|---|---|---|---|---|---|
| 19 | DPG | 400 | 148.5 | — | — | 6 | + trace MeONa | — | — |
| 20 | DEG | 300 | — | 26 | 43.5 | 3 | — | — | + |
| 21 | " | " | — | 24.6 | 41 | 4.5 | — | — | with BDG |
| 22 | " | 320 | — | 24.6 | 41 | 3 | — | — | + |
| 23 | DEG | 1200 | 720 | — | — | 6 | — | — | — |
| 24 | BDG | 206 | 93 | — | — | 5 | — | 72 | + |
| 25 | DEG | 300 | — | 30 | 47 | 5 | — | + | — |
| 26 | " | " | — | 36.8 | 61.2 | 3.25 | — | — | — |
| 27 | " | 180 | — | 36.8 | 61 | 3 | — | — | — |
| 28 | " | 150 | — | 23.8 | 40 | 3 | — | — | — |

DEG = Diethylene glycol
BDG = butyl diglycol
DPG = Dipropylene glycol
MeONa = sodium methylate

Analysis / Solubility

| Example No. | Index Of Hydroxylated Amine of The Invention Found (meq/g) | Theoretical | Index Of Saponification Found* | Solubility In acidified Water |
|---|---|---|---|---|
| 19 | | | | + |
| 20 | 2 | 2.06 | 0.25 | + |
| 21 | 1.8 | 2 | 0.14 | + |
| 22 | 1.85 | 1.89 | 0.17 | + |

TABLE I-continued

| | | | | |
|---|---|---|---|---|
| 23 | | | 0.39 | + |
| 24 | 1.65 | 1.60 | 0 | + |
| 25 | 1.9 | 1.80 | 0.38 | (Cloudy) |
| 26 | 1.97 | 1.89 | 0.5 | + |
| 27 | 1.96 | 2 | 0.23 | + |
| 28 | 1.9–2 | 1.8 | 0.38 | + |

*Theoretical Index Of Saponification = 0

III. Surface Active Agents Which Are The Condensation Product Of An Alcohol, An Epoxide And Glycerol Epihalohydrin In accordance with this embodiment of the present invention there are provided cationic surface-active agents selected from the group consisting of:

1. agents having the formula:

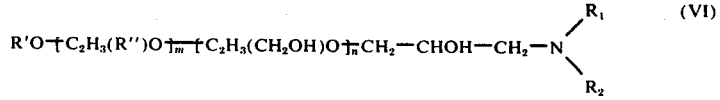
(VI)

which are hydroxylated condensation products of an alcohol having the formula R'OH, an epoxide having the formula

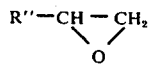

and glycerol epihalohydrin, wherein R' is a hydrophilic group selected from the class consisting of linear or branched alkyl and alkenyl having 12–20 carbon atoms, R'' represents a member selected from the group consisting of methyl and ethyl, m has a statistical average value of 2–6, $R_1$ and $R_2$ each independently are selected from the group consisting of lower alkyl having 1–4 carbon atoms, lower hydroxyalkyl having 1–4 carbon atoms or together with the nitrogen atom to which they are attached form a ring selected from the group consisting of morpholine and piperidine and n has a statistical average value of 0.5–4; and 2. agents which are the quaternary ammonium salts of (1) having the formula

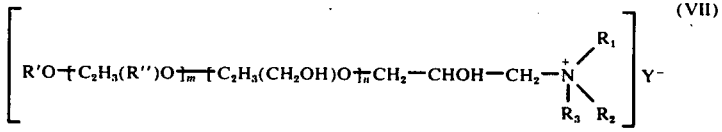
(VII)

wherein R', R'', $R_1$, $R_2$, m and n have the meaning given above, $R_3$ is selected from the group consisting of methyl and ethyl and Y is an anion selected from the group consisting of Cl, Br, I, $SO_4CH_3$, $SO_4C_2H_5$, $CH_3SO_3$ and

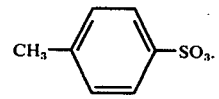

The cationic surface active agents of this embodiment of the present invention are prepared by a. condensing on a fatty alcohol having the formula R'OH wherein R' has the meaning given above, m moles of an epoxide or mixture of epoxides having the formula

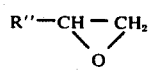

wherein R'' has the meaning given above to form a compound having the formula $$R'O\text{—}\{C_2H_3(R'')O\}_mH \quad (VIII);$$

b. condensing on the compound represented by formula VIII, (n+1) moles of glycerol epihalohydrin having the formula

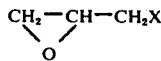

wherein n has the meaning given above and X is halogen, preferably chlorine or bromine to form a mixture of polyhalogenated polyethers having the formula $$R'O\text{—}\{C_2H_3(R'')O\}_m\{C_2H_3(CH_2X)O\}_nCH_2\text{—}CHOH\text{—}CH_2\text{—}X \quad (IX);$$

c. dehydrohalogenating said polyhalogenated polyethers from step (b) with an alkali metal or an alkaline earth metal hydroxide to form a mixture of polyhalogenated glycidyl ethers having the formula

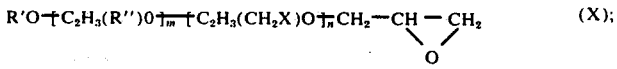
(X);

d. reacting the polyhalogenated glycidyl ethers from step (c) with a secondary amine to form a mixture of polyhalogenated tertiary amines having the formula

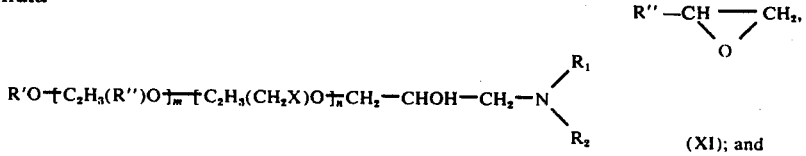

and e. replacing the halogen by hydroxyl in the polyhalogenated tertiary amines from step (d) to form a mixture of polyhydroxylated tertiary amines having formula VI given above.

The various steps in the above process for preparing the surface active agents represented by formula VI are as follows:

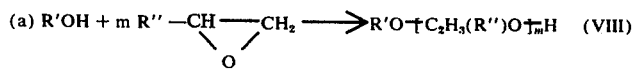

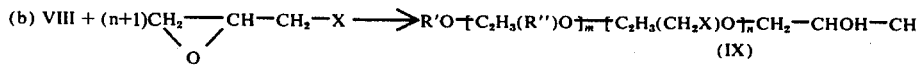

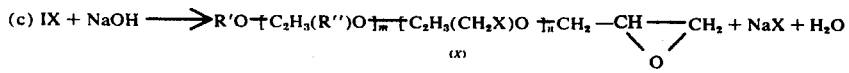

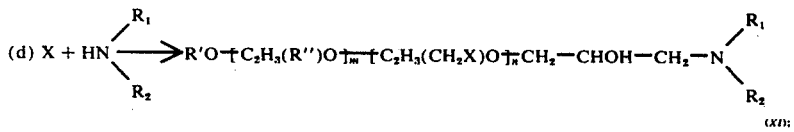

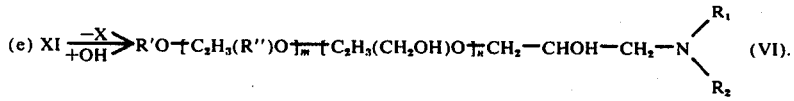

The quaternization of the surface-active agents represented by formula VI yields quaternary ammonium salts having the formula

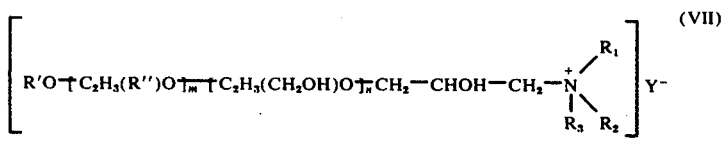

wherein R′, R″, R$_1$, R$_2$, R$_3$, Y$^-$, m and n have the meaning given above.

In the course of the condensation reaction (a) and (b) above, when the epoxy ring is opened during the polycondensation, a mixture of compounds comprising the structure

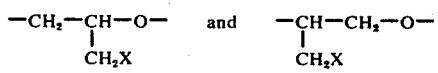

is obtained.

Thus a mixture of compounds having the general structure —C$_2$H$_3$(CH$_2$X)O— is obtained. Consequently, the hydroxylated compound of formulae VI and VII given above represents four isomers of each, two of which result from the opening of the epoxide

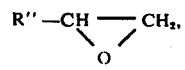

the other two resulting from the epoxide group of the glycerol epihalohydrin.

In the above formulae m is defined by the equation:

$$m = \frac{56,000 - M'I'}{E'I'}$$

wherein M′ is equal to the molecular weight of the alcohol R′OH, E′ is equal to the molecular weight of the epoxide

R″—CH—CH$_2$
\\ /
O and I′ is the hydroxyl index of the condensation product, i.e., the compound represented by formula VIII above, after step (a).

In the same formula above, n is defined by the equation:

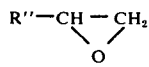

$$(n + 1) = \frac{56,000 - IM}{IE}$$

wherein M is equal to the molecular weight of the alcohol of formula VIII, E is equal to the molecular weight of the glycerol epihalohydrin and I is the hydroxyl index of the condensation product, i.e., the mixture of polyhalogenated polyethers represented by formula IX, after step (b).

During the condensation reaction (a) in which m moles of the epoxide having formula $$R'' - \underset{\underset{O}{\diagdown\diagup}}{CH} - CH_2$$

which epoxide can be for instance propylene oxide and/or butylene oxide, are reacted on one mole of alcohol having the formula R'OH, the number of moles of epoxide fixed by one mole of alcohol to form the recurring units $-\!\!+\!C_2H_3(R'')O\!+\!-$ can be greater or smaller than the value m and a mixture of compounds, all responding to general formula VIII are formed, but in which the number of recurring units varies and all those different numbers are distributed statistically around a mean value represented by m. Consequently m in the final product represents the mean value or the average statistical value of the number of recurring units $-\!\!+\!C_2H_3(R'')O\!+\!-$ fixed on the different compounds having the general formula (VI) or VII.

During the condensation reaction (b) in which (n+1) moles of glycerol epihalohydrin are reacted on one mole of alcohol $R'O-\!\!+\!C_2H_3(R'')O\!+\!-H$ designated as formula VIII the number of moles of glycerol epihalohydrin fixed by one mole of alcohol VIII to form the recurring units $-\!\!+\!C_2H_3(CH_2OH)O\!+\!-$ can be greater or smaller than the value n and a mixture of compounds, all responding to general formula IX are formed, but in which the number of recurring units $-\!\!+\!C_2H_3(CH_2OH)O\!+\!-$ varies and all those different numbers are distributed statistically around a mean value represented by n. Consequently n in the final product represents the mean value or the average statistical value of the number of recurring units $-\!\!+\!C_2H_3(CH_2OH)O\!+\!-$ fixed on the different compounds having the general formula VI or VII.

An important fact which should be emphasized and which constitutes one of the essential advantages of the process of preparing the surface-active agents of this invention is that the present process results in the formation of compounds having a single lipophile chain per hydrophile chain.

Moreover, the process of the present invention permits the regulation of the hydrophilic and lipophilic properties of the final product. The hydrophilic characteristic of the resulting surface-active agents can be regulated by choosing the value of the number n of moles of glycerol epihalohydrin reacted with one mole of fatty alcohol. The lipophilic characteristics of the resulting surface-active agents can be regulated by choosing the length of the hydrocarbon chain R in the fatty alcohol.

The following is a detailed description of a preferred embodiment of producing the above surface-active agents.

In steps (a) and (b), i.e., the condensation of propylene and/or butylene oxide on one hand and of glycerol epichlorohydrin or epibromohydrin on the other hand, are carried out, one after the other, in the presence of an acid catalyst such as boron trifluoride, stannic chloride or antimony pentachloride, at a temperature of between 25° and 160° C and preferably between 60° and 120° C if boron trifluoride is used. The proportion of $BF_3$ with respect to the total mass of the reactants is between 0.1 and 1% by weight.

In step (c) the polyhalogenated polyethers represented by formula (IX) above, which result from step (b), are converted to glycidyl ethers (formula X) by dehydrohalogenation of the halohydrin, using an aqueous solution of an alkali or alkaline earth metal hydroxide, having a concentration, by weight, of from 20 to 50%. The molar ratio of alkali or alkaline earth metal hydroxide to polyhalogenated polyethers ranges between 1:1 and 1:2 and preferably from about 1:2.2 to 1:1.5. During this phase of the overall process, which ordinarily is initially conducted at about 20° C or ambient temperature, the reaction temperature rises to about 100° C. When the exothermicity of the reaction ceases, the reaction is terminated by heating the reaction mixture in a water bath. This dehydrohalogenation operation is generally conducted in the presence of a solvent to obtain high reaction speeds and high epoxidation yields. The solvent employed should preferably, not be miscible with concentrated aqueous solutions of electrolytes so that the resulting polyhalogenated glycidyl ethers can be separated from the reaction medium simply by decantation. Tertiary butyl alcohol and 2-butoxy ethanol are particularly useful solvents when used in weight proportions essentially equal to that of the halohydrin to be dehydrohalogenated. Quaternary ammonium salts comprising a lipophile chain can be used to improve the contact between the reactants. The resulting polyhalogenated glycidyl ethers if desired, can be isolated by evaporation of the solvent or it can be used in solution in the subsequent stage, i.e., step (d).

In a step (d) the polyhalogenated glycidyl ethers from step (c) are reacted with a secondary amine at temperatures of from 25° to 120° C to open the epoxide ring and thereby from the polyhalogenated tertiary amines having formula XI.

Alternatively the polyhalogenated tertiary amines of formula XI can be obtained in a single step by reacting the polyhalogenated polyethers from step (b) directly with a secondary amine in the presence of an alkali or alkaline earth metal hydroxide.

Representative secondary amines usefully employed in the present invention include diethylamine, dipropylamine, morpholine, piperidine, and alkanolamines such as diethanolamine, diisopropanolamine, diglycerylamine and N-ethylethanolamine.

The molar ratio of secondary amine to epoxide (when the glycidyl ethers responding to formula IX are isolated) and the molar ratio of secondary amine: halohydrin (when the secondary amine is reacted directly without isolating the glycidyl ethers responding to formula IX) are between about 1:1 and 1:1.5, the preferred ratio being about 1:1.5.

In step (e) the replacement of the halogen by a hydroxyl in the polyhalogenated tertiary amine from step (d), or from its alternate route, yields the polyhydroxylated amines of the present invention which are useful surfaceactive agents and which are represented by formula VI. This operation is carried out with an alkaline salt of carboxylic acid, such as sodium or potassium acetate, at a temperature of between 150° and 200° C, preferably, about 180° C, in the presence or absence of a solvent.

The presence of a solvent in the reaction medium during step (e) assures both instantaneous and progressive contact among the reactants and easy separation therefrom of the mineral halide formed. Suitable solvents include ethylene glycol, diethylene glycol, propylene glycol, dipropylene glycol, as well as the monoalkylethers of these diols, such as monobutyl ether of ethylene glycol and monobutyl ether of diethylene glycol. The hydroxylated solvents also intervene by alcoholysis of the esters formed in an intermediate step.

When the reaction is carried out in the absence of a solvent, as may be the case when the alkaline salt of carboxylic acid is somewhat soluble in the reaction medium, the polyhydroxylated tertiary amine is obtained by alcoholysis of the esters of carboxylic acid with a lower alcohol such as methanol or ethanol, or by saponification followed by salting out or extraction.

In one preferred commercial embodiment, the polyhalogenated polyethers from steps (a) and (b) are reacted with a secondary amine, as defined above in the presence of an alkali or alkaline earth metal hydroxide, without isolating the glycidyl ethers thus formed. After reaction with an alkaline salt of carboxylic acid, the esterified amino ethers are separated from the mineral halide by filtration or washing, and then the salts of carboxylic acid are regenerated in situ from the carboxylic esters by saponification with an alkaline hydroxide. Thus, the alkaline salt of carboxylic acid is recovered in aqueous solution and can be used for another hydroxylation reaction.

As stated above, the surface-active agents of this embodiment of the present invention also include the quaternary ammonium salts of the compounds represented by formula VI, the quaternary ammonium salts being represented by formula VII. To produce said quaternary ammonium salts, the compounds represented by formula VI can be reacted with, for instance, a quaternizing agent such as methyl sulfate, ethyl sulfate, ethyl chloride, ethyl bromide, methyl iodide, methyl paratoluylene sulfate or methyl methane sulfonate. The mole ratio of quaternizing agent to the compounds represented by formula VI corresponds to the stoichiometric amount or is slightly inferior and the reaction is carried out at a temperature ranging from about 15 to 100° C at atmospheric pressure.

Compared, for example, with fatty amines, the surface-active agents of this embodiment of the present invention lack the odor characteristic of fatty amines and their derivatives, have a low melting point, are saturated and consequently do not become rancid.

Additionally, the process of the present invention yields stable surface-active agents which are soluble in water without the introduction of supplementary ionic groups, and especially anionic groups which impair the substantive characteristics of the surface-active agents. Further, the surface-active agents of this invention are considerably less irritating to the skin and to mucous membranes than are the fatty amines and their derivatives.

The surface-active agents of the present invention also compare favorably with amino polyethers having the formula

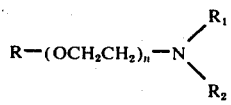

and the substitution of a $+C_2H_3(CH_2OH)O+$ group for the oxyethylene group $+OCH_2CH_2+$ is very useful.

The surface-active agents of this invention, because of their physical and chemical characteristics, are suitably employed in cosmetic preparations, shampoos, permanent waving compositions and particularly in hair dye and hair rinse compositions. Further, when the surface active agents of this embodiment of the present invention, and especially those represented by formula VI are used in compositions for treating hair, they impart to the hair a certain sheen and a pleasing texture. The hair is particularly soft, odorless and is easily untangled.

Thus, in accordance with the present invention there is provided a shampoo composition comprising an aqueous solution of the surface active agents of this invention present in amounts of about 0.5 to 6 percent by weight of said shampoo composition, having a pH ranging from about 3 to 6.5. The pH can be adjusted to the desired value by incorporating into said composition an acidic component such as lactic, acetic or citric acid and the like.

In another embodiment of the present invention hair is permanently waved by applying to the hair wound on curlers during the first stage, i.e., during the reducing stage, a composition comprising reducing agent, permitting the composition to remain on the hair for a time sufficient to alter the disulphide bonds of the keratin of the hair, generally about 10–40 minutes, thoroughly rinsing the hair to remove residual reducing agent and applying in the second stage, i.e., during the neutralization stage, a cosmetic composition comprising a mixture of an oxidizing or neutralizing agent and the surface-active agent of the present invention, whereby the disulphide bonds of the keratin of the hair are reformed.

Conventional reducing agents employed are advantageously those organic thiols which are generally used to perform the first stage of a permanent waving operation. Representative thiols include thioglycolic acid and its salts, glycol thioglycolate, glycerol thioglycolate, thioglycolic amide, thiolactic acid, glycol thiolactate, β-mercaptoethanol, N-carboxymethyl mercapto acetamide, β-mercapto propionic acid, and the like. Generally the composition comprising the reducing agent is an aqueous solution of said reducing agent present in amounts of about 2 to 15 percent by weight thereof and having a pH ranging from about 8 to 10.

The neutralizing composition of the present invention comprises an aqueous solution of 0.5 to 4 weight percent of a conventional neutralizing or oxidizing agent and about 0.2 to 15 weight percent of the surface-active agent of this invention. Conventional neutralizing agents employed include, for instance, hydrogen peroxide, sodium or potassium bromate, sodium perborate or percarbonate and the like.

The surface-active agents of the present invention are also usefully employed in hair dye compositions comprising a solution in a solvent selected from the group consisting of water and an aqueous solution of a lower alkanol such as ethanol and isopropanol, of a glycol such as butyl glycol, propylene glycol, ethylene glycol, 3-amyloxy 4-propane 1,2-diol and of a monoalkyl ether of glycol such as monobutyl ether of ethylene glycol wherein said alkanol and/or glycol and/or ether of glycol is present in amounts of about 8 to 25 percent by weight of said solution, a hair dye such as azo, anthraquinone and nitro dyes of the benzene series, and 0.5 to 6 percent by weight of the surface-active agent of the present invention.

Additionally, if desired, said hair dye composition can include its weight of hydrogen peroxide to provide said composition in gel form.

Generally the dye is present in amounts of about 0.1 to 5 percent by weight of said composition which has a pH ranging from about 8 to 10.5.

Representative dyes include paraphenylene diamine, 2,5-toluene diamine sulfate, chloroparaphenylene diamine sulfate, nitroparaphenylene diamine, 1,2,4-triaminobenzene trihydrochloride, paraaminodiphenyl amino, ortho phenylene diamino, 4-chloro ortho phenylene diamine, 4-nitro ortho phenylene diamine, paraaminophenol, 4-amino 2-methyl phenol sulfate, 4-amino-3-methyl phenol, 4-amino 2-nitro phenol, m-diamino anisol and its sulfate, p-aminophenol and its sulfate, nitro-p-phenylene diamine, p-toluylene diamine, resorcine, hydroquinone, 3-nitro 4-β-aminoothylamino anisole hydrochloride, 2,4-diaminophenol hydrochloride, paramethyl aminophenol sulfate, ortho aminophenol, 4-chloro 2-aminophenol, 4-nitro 2-aminophenol, 5-nitro 2-aminophenol, 4,6-dinitro 2-aminophenol, 6-chloro 4-nitro 2-aminophenol hydrochloride, 4-amino diphenylamine, 4,4'-diamino diphenylamine sulfate, metaphenylene diamine, chloro-meta phenylene diamine, nitro-meta phenylene diamine, meta toluylene diamino, 2,4-diamino anisol sulfate, meta aminophenol, 3,5-diaminophenol hydrochloride, diethyl meta aminophenol, paraamino ortho cresol, 1-dimethylamino 3-amino ethylamino 4-nitro benzene, 1-hydroxy-2,4-di(p-trimethylammoniumphenylamino) anthraquinone methosulfate, 1-hydroxy-2,4-di(p-trimethyl-ammoniumphenylamino) anthraquinone iodide, 1-amino propylamino anthraquinone, 1,8-Bis-γ-aminopropylamino anthraquinone, 1-diethylamino2-ethylamino-nitro-4-NN-dihydroxyethylamino benzene dihydrochloride, 4-N-methylamino-3-nitro-1-N--aminoethylamino benzene, [1-hydroxy-4-(γ methylmorpholinium) propylamino anthraquinone] methyl sulfate, 2-β-aminoethylaminoanthraquinone, 1,5-di-(β-aminopropylamino) anthraquinone, 1-methylamino-4-amino propylamino anthraquinone, 1-amino propylamino-anthraquinone 1,4-diamino-5-γ amino propylamino-anthraquinone. Additional examples of commercially available useful dyes include, as monoazo dyes, Cl Acid Blue 92 (13390) and Cl Acid Yellow 23 (19140); as diazo dyes, Cl Acid Orange 24 (20170); as triphenylmethane type dyes, Cl Acid Blue 1 (42045), Cl Acid Violet 19 (42685), Cl Acid Blue 22 (42755) and Cl Acid Violet 15 (43525); as xanthene dyes, Cl Acid Violet 9 (45190); as azine dyes, Cl Acid Black 2 (50420), Cl Acid blue 59 (50315) and Cl Acid Blue 61 (50330); as anthraquinone dyes, Cl Acid Violet 43 (60730), Cl Acid Blue 80 (61585), Cl Acid Violet 51 (62165) and Cl Acid Blue 138 (62075); as premetallized dyes, both 1:1 and 2:1 complexes, chromium and cobalt, for instance Cl Disperse Blue 14 (61500), Cl Disperse Blue 6 (62050) and Cl Disperse Blue 31 (64505); as direct dyes, Cl Direct Blue 2 (22590), Cl Direct Black 51 (27720) and Cl Direct Violet 51 (27905); and as solvent dyes, (15680) and Cl Solvent Violet 10 (45190).

The surface-active agents of the present invention are also usefully used in hair rinses. These hair rinses are employed on the hair in order to make easier its disentanglement, especially when same is electric or curly. These hair rinses comprise a solution in a solvent selected from the group consisting of water and an aqueous solution of a lower alkanol such as ethanol and isopropanol wherein said alkanol is present in amounts of about 15 to 60% by weight of said solution, a cosmetic resin in amounts of about 0.5 to 5% and 0.1 to 2% by weight of the surface-active agents of the present invention. This composition may also comprise a perfume in amounts of about 0.05 to 0.5% and hair dyes from an amount of about 0.005 to 3% of said composition which has a pH from about 7 to 8.5 Representative cosmetic resins include polymers, i.e. polyvinyl pyrrolidene (PVP) having a molecular weight ranging between 40,000 to 360,000 the preferred molecular weight being 40,000, or copolymers such as the copolymer of vinyl pyrrolidone and vinyl acetate (MV = 40,000 – 160,000 ) 70% : 30% to 30% : 70%, the preferred proportion being 60% : 40% having a viscosity of 3.3 to 4 centipoises in 5% solution in ethanol; or copolymers of crotonic acid and vinyl acetate 90% : 10% having a molecular weight of 40,000 to 200,000 and preferably of 50,000 and a viscosity of 7 to 9 centipoises in 5% solution in tetrachloroethane; or monoalkyl ester of the copolymer of methylvinyl ether and maleic acid.

Representative hair dyes include direct dyes such as azo dyes, triphenylmethane type dyes, xanthene dyes, anthraquinone dyes, azine dyes, premetallized dyes, solvent dyes and the like. All the above cited dyes as commercially available useful dyes may be used.

In use, the compounds of the present invention can be in the form of salts of inorganic and organic acids such as hydrochloric, phosphoric, boric, acetic, citric and lactic acids.

IV. Preparation Of Surface-Active Agents Which Are The Condensation Product Of An Alcohol, An Epoxide And Glycerol Epihalohydrin

EXAMPLE 29

Preparation of a mixture of surface-active agents having the formula

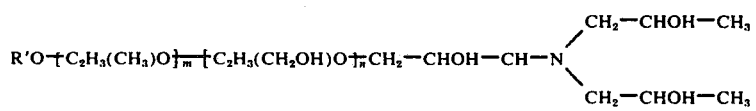

wherein R' is octadecyl, $m$ has a statistical average value of 5.25 and $n$ has a statistical average value of 1.

Steps (a) and (b) Poly addition of propylene oxide and glycerol epichlorohydrin on stearoyl alcohol 6.25 ml of an acetic acid complex of boron fluoride at 36% $BF_3$ are added to a molar equivalent quantity of industrial stearoyl alcohol (hydroxyl index: 195 mg KOH/g) dehydrated by heating in a boiling water bath in a vacuum and melted.

The mixture is heated to 75°–80° C. Then 5.25 moles of propylene oxide are added drop by drop, the rate of flow being regulated so that the temperature stays between 75°–80° C because of the exothermic nature of the reaction. When the propylene oxide has been completely used up, which is determinated by measurement of the epoxide function in a sample withdrawn for the purpose, 2 moles of glycerol epichlorohydrin are added drop by drop. The temperature is kept constant as before by regulating the rate of addition. The polychlorinated polyether having the following formula is obtained:

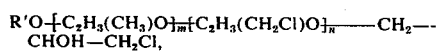
CHOH—CH₂Cl, wherein R', m and n have the meaning given above, the said polyether having a theoretical hydroxyl index of 73.5 (found 90) mg KOH/g.

Steps (c) and (d) dehydrohalogenation and reacton with a secondary amine 177 g of diisopropanolamine, then 143 g of a 40% sodium hydroxide solution are added to 776 g of the above polychlorinated polyether.

When the reaction ceases to be exothermic, the mixture is heated to 90°–95° C for 3 hours.

A mixture of polychlorinated tertiary amines having the following formula is thus obtained:

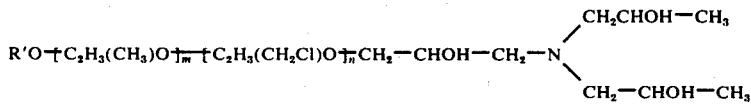

wherein R', m and n have the meaning given above.

Step (e) hydroxylation

The excess sodium hydroxide is neutralized with 8 ml of anhydrous acetic acid. 800 ml of butyl monoether of diethylene glycol and 108 g of potassium acetate are added. After the water has been removed, the mixture is heated to 180°–185° C for 5 hours.

After cooling to 95° C, 1.8 liters of hot water are added, the mixture is stirred and decanted and the aqueous phase containing the sodium chloride which has formed is drawn off.

The water and solvent are evaporated from the organic phase by progressively raising the temperature to 180° C under a pressure of 15 to 20 mm of mercury.

An oily yellow product is obtained which is soluble in warm at a pH of 3 (the pH being adjusted with lactic acid). Its formula is given at the top of this example.

This product can also be obtained with the same results by using the same reactant in the same proportions, but no solvent. In this case, the product is deacetylated by saponification, then separated by salting out.

EXAMPLE 30

The procedures of Example 29 are repeated except that comparably equivalent amounts of butylene oxide are employed in steps (a) and (b) rather than propylene oxide.

EXAMPLE 31

The procedures of Example 29 are repeated except that comparably equivalent amounts of glycerol epibromohydrin are employed in steps (a) and (b) rather than glycerol epichlorohydrin.

EXAMPLES 32–38

The procedures of Example 29 are repeated except that comparably equivalent amounts of diethylamine (Ex. 32), morpholine (Ex. 33), piperidine (Ex. 34), diethanolamine (Ex. 35), dipropylamine (Ex. 36), diglycerylamine (Ex. 37) and N-ethylethanolamine (Ex. 38) are employed in step (d) rather than diisopropanolamine.

EXAMPLE 39

A mixture of surface-active agents having the following formula is prepared:

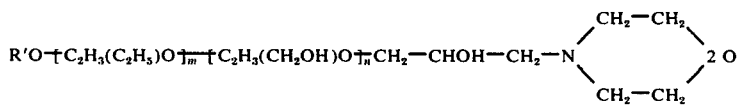

wherein R' is alkyl having 16–18 carbon atoms, m has a statistical average value of 3 and n has a statistical average value of 1.

Proceeding as in Example 29, in steps (a) and (b) there are employed rather than stearoyl alcohol and propylene oxide, a mixture of fatty alcohols containing essentially cetyl alcohol and stearyl alcohol having the following properties: hydroxyl index, 211; iodine index, 0.5 and fusion point, 52.5° C; and butylene oxide, respectively, to produce the following polychlorinated polyether,

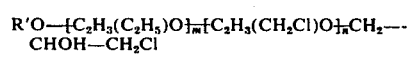

wherein R', m and n have the meaning given above.

Then, 36.5 g of morpholine and 44 g of a 40% aqueous solution of sodium hydroxide are added to 222 g of the above polychlorinated polyether. The addition of the sodium hydroxide takes 15 minutes and the resulting mixture is then heated in a water bath for three hours. A polychlorinated tertiary amine having the following formula is thus obtained,

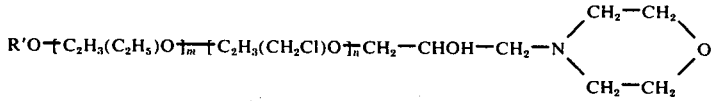

The excess sodium hydroxide is neutralized with 2.4 g of glacial acetic acid and the reaction mixture is diluted with an equivalent weight of dipropylene glycol. Then 35 g of anhydrous potassium acetate are added and the mixture is heated to 180°–185° C for five hours after the water has been removed.

After evaporation of dipropylene glycol under reduced pressure, the de-acetylation is completed by saponification using 5 g of an aqueous 40% solution of sodium hydroxide. It is then washed twice with 250 ml of boiling water and the organic phase is then dehydrated by being heated in a vacuum. 211 g of a red-brown oil, having the formula given at the beginning of the example, are collected.

EXAMPLE 40

Preparation of a mixture of surface-active agents having the formula

wherein R' is dodecyl, $m$ has a statistical average value of 2 and $n$ has a statistical average value of 4.

Steps (a) and (b) Polyaddition of propylene oxide and glycerol and epichlorohydrin on dodecyl alcohol.

0.8 ml of an acetic acid complex of boron fluoride at 36% $BF_3$ are added to 0.2 mole (37.2 g) of industrial dodecyl alcohol.

The mixture is heated to 75°–80° C. Then 0.4 mole of propylene oxide are added drop by drop, the rate of flow being regulated so that the temperature stays between 75°–80° C because of the exothermic nature of the reaction. When the propylene oxide has been completely used up, which is determined by measurement of the epoxide function is a sample withdrawn for the purpose, 1 mole (92.5 g) of glycerol epichlorohydrin is added drop by drop. The temperature is kept constant as before by regulating the rate of addition. The polychlorinated polyether having the following formula is obtained:

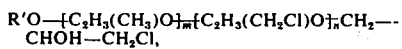

wherein R', $m$ and $n$ have the meaning given above, the said polyether having a theoretical hydroxyl index of 73 mg KOH/g.

Steps (c) and (d) dehydrohalogenation and reaction with a secondary amine 22.5 g of diethanolamine, then 22 g of a 40% sodium hydroxide solution are added to 0.2 mole (103 g) of the above polychlorinated polyether.

When the reaction ceases to be exothermic, the mixture is heated to 90°–95° C for 2 hours.

A mixture of polychlorinated tertiary amines having the following formula is thus obtained:

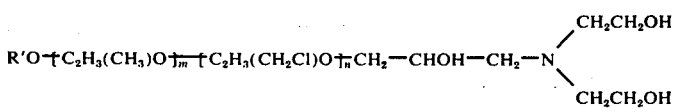

wherein R', $m$ and $n$ have the meaning given above.

Step (e) hydroxylation 110 g of dipropylene glycol and 44 g of potassium acetate are added. After the water has been removed, the mixture is heated to 180–185° C for 4 hours.

The potassium chloride which has formed is eliminated by filtration and the dipropylene glycol is evaporated under vacuum.

In order to complete the de-acetylation the crude product is dissolved in 125 ml of absolute ethyl alcohol to which 1 ml of a 25% solution of sodium methylate in methanol has been added.

After one night at room temperature the product is filtrated. Alcohol and the ethyl acetate which has formed are drawn off.

A brown viscous oily product is obtained which is soluble in water and the formula of which is represented above.

EXAMPLE 40 A

The procedures of Example 40 are repeated except that comparably equivalent amounts of butylene oxide are employed in steps (a) and (b) rather than propylene oxide.

EXAMPLE 40 B

The procedures of Example 40 are repeated except that comparably equivalent amounts of glycerol epibromohydrin are employed in steps (a) and (b) rather than glycerol epichlorohydrin.

EXAMPLES 40 C – 40 J

The procedures of Example 40 are repeated except that comparably equivalent amounts of diethylamine (Ex. 40 C), morpholine (Ex. 40-D), piperidine (Ex. 40 E), diisopropanolamine (Ex. 40 F), dipropylamine (Ex. 40 G), diglycerylamine (Ex. 40 H) and N-ethylethanolamine (Ex. 40 J) are employed in step (d) rather than diisopropanolamine.

V. Cosmetic Compositions Utilizing As A Component Thereof Surface-Active Agents Of The Present Invention

EXAMPLE 41

After application of a conventional permanent-waving composition consisting of an aqueous solution of 8% ammonium thioglycolate having a pH of 9.5, the hair is rinsed and 100 cm³ of the following solution are applied in the usual manner:

| | |
|---|---|
| $C_{12}H_{25}O \pend{+}C_2H_3(CH_2OH)O\pend{+}_n CH_2-CHOH-CH_2-N\begin{smallmatrix}CH_2-CHOH-CH_3\\ \\ CH_2-CHOH-CH_3\end{smallmatrix}$ | 2 g |
| Phosphoric acid | 1.2 g |
| Hydrogen peroxide, q.s.p. | 7 volumes |
| Water, q.s.p. | 100 cm³ |

It is noted that the application is simple, the lather goes on easily, it holds well on the curlers, rinses easily and after unrolling, the hair is particularly soft, shiny and odorless and untangles easily.

EXAMPLE 42

After reduction of the hair with an aqueous solution of the same composition as that above, the hair is rinsed and a solution having the following formula is applied as a fixative:

| | |
|---|---|
| $RO\pend{+}C_2H_3(CH_2OH)O\pend{+}_n CH_2-CHOH-CH_2-N\begin{smallmatrix}CH_2-CH_2-OH\\ \\ CH_2-CH_2-OH\end{smallmatrix}$ | 1.2 g | wherein $R = C_{12}-C_{14}$ and $n$ has a statistical average value of 0.5.

| | |
|---|---|
| Lactic acid, q.s.p. | pH = 3.5 |
| Hydrogen peroxide, q.s.p. | 6 volume |
| Water q.s.p. | 100 cm³ |

It will be noted that, as above, the hair is soft, shiny and odorless, and that it combs out and untangles easily.

EXAMPLE 43

After reduction of the hair with a permanent waving composition having the following composition: thioglycolic acid

| | |
|---|---|
| Thioglycolic acid | 10 g |
| Ammonium sesquicarbonate | 10 g |
| Ammonia, q.s.p. | pH = 8.5 |
| Water, q.s.p. | 100 cm³ |

The hair is left for a while, and then rinsed. A fixative having the following composition is then applied:

| | |
|---|---|
| $RO\pend{+}C_2H_3(CH_2OH)O\pend{+}_n CH_2-CHOH-CH_2-N\begin{smallmatrix}CH_2-CH_2-OH\\ \\ CH_2-CH_2-OH\end{smallmatrix}$ | 3 g | wherein $R = C_{12}-C_{14}$ and $n$ has a statistical average value of 1.

| | |
|---|---|
| Phosphoric acid | 1.5 g |
| Hydrogen peroxide, q.s.p. | 6 volumes |
| Water, q.s.p. | 100 cm³ |

After letting the setting agent act for a certain time, and rinsing, the hair is in very good shape, it untangles easily, is soft, and there is no foam left in it. These improvements in rinsing are due to the presence of the mixture of the compounds which is the object of the present invention and to the fact that this mixture of compounds is highly hydrophilic due to the increase in the value of $n$ from 0.5 to 1.

EXAMPLE 44

After using the same permanent waving composition as before, the following solution is applied as a fixative:

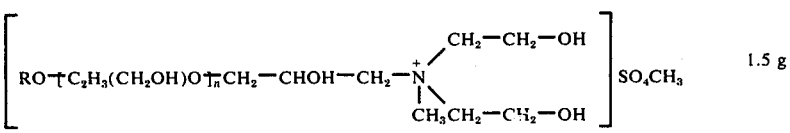

| | 1.5 g |
|---|---| wherein R is a straight chain alkyl having 12 to 14 carbon atoms and n has a statistical average value of 0.5.

| | |
|---|---|
| Citric acid | 0.1 g |
| Hydrogen peroxide, q.s.p. | 5 volumes |
| Water, q.s.p. | 100 cm³ |

The results are excellent. Rinsing is facilitated and softness of the hair is particularly pleasing. This is due to the fact that a quaternary derivative has been used instead of a tertiary as before, and this type of derivative has a greater affinity for hair and makes it softer and shinier.

EXAMPLE 45

A solution having the following composition is prepared:

| | |
|---|---|
| RO⁻ｔC₂H₃O(CH₂OH)ｔₙH<br>(R = 9-octadecenyl n has a statistical average value of 2) | 25 g |
| RO⁻ｔC₂H₃O(CH₂OH)ｔₙH<br>(R = 9-octadecenyl n has a statistical average value of 4) | 15 g |
| Oleic acid | 3 g |
| RO⁻ｔC₂H₃(CH₂OH)Oｔₙ CH₂—CHOH—CH₂—N(CH₂—CH₂—OH)(CH₂—CH₂—OH)<br>(R = octadecenyl n has a statistical value of 1) | 3 g |
| Butylcellosolve | 8 g |
| Ethanol | 5 g |
| Propylene glycol | 5 g |
| Trilon B (sodium salt of ethylenediamine tetracetic acid) | 0.3 g |
| Paratolylenediamine | 1 g |
| Meta diamino anisol sulfate | 0.05 g |
| Meta aminophenol | 0.15 g |
| Para aminophenol | 0.1 g |
| 20% ammonia | 13 g |
| Water, q.s.p. | 100 cm³ |

To obtain the gel necessary for dyeing hair it is mixed with equal parts of hydrogen peroxide at 20 volumes. This gel is applied to the hair, left for 30 minutes, rinsed and washed.

A chestnut shade is obtained.

EXAMPLE 46

A solution having the following composition is prepared:

| | |
|---|---|
| Nonylphenol oxyethylenated with 4 moles ethylene oxide | 25 g |
| Nonylphenol oxyethylenated with 9 moles ethylene oxide | 15 g |
| Oleic acid | 3 g |
| RO⁻ｔC₂H₃(CH₂OH)Oｔₙ CH₂—CHOH—CH₂—N(CH₂—CH₂—OH)(CH₂—CH₂—OH)<br>wherein R is 9-octadecenyl and n has a statistical average value of 1. | 3 g |
| Butyl cellosolve | 10 g |
| Ethanol | 8 g |
| Trilon B (sodium salt of ethylenediamine tetracetic acid) | 0.3 g |
| Paratolylene diamine | 1 g |
| Meta diamino anisol sulfate | 0.05 g |
| Meta aminophenol | 0.15 g |
| Para aminophenol | 0.1 g |
| 20% concentration ammonia | 13 g |
| Water, q.s.p. | 100 cm³ |

To obtain a gel, the above mixture is further admixed with equal parts of hydrogen peroxide at 20 volumes. The resulting gel is applied to the hair, left for 30 minutes, rinsed and washed. A chestnut shade is obtained.

EXAMPLE 47

A solution having the following composition is prepared:

| | |
|---|---|
| 4-amino-3-nitro-1-N-(B-diethylaminoethyl) amino benzene | 0.5 g |

-continued

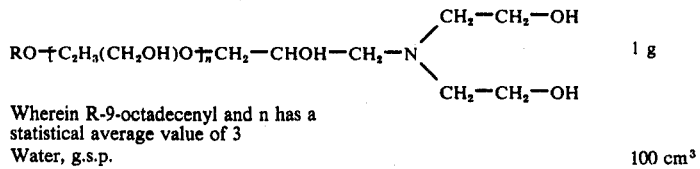
1 g

Wherein R-9-octadecenyl and n has a
statistical average value of 3
Water, g.s.p.                100 cm³

The chestnut or light chestnut colored hair is treated directly with this solution by applying the same thereto and permitting it to remain in contact with the hair for 30 minutes. Thereafter the hair is rinsed and washed and there is imparted thereto a violet mahogany shade.

EXAMPLE 48

An aqueous solution having the following composition is prepared:

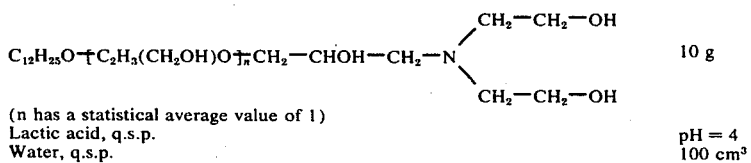
10 g (n has a statistical average value of 1)
Lactic acid, q.s.p.            pH = 4
Water, q.s.p.              100 cm³

10 cm³ of this solution are applied to previously dampened hair and the hair is vigorously rubbed to emulsify all the dirt. The hair is rinsed thoroughly with water, then another 8 to 10 cm³ of the product are applied. An abundant lather is obtained and the hair is rinsed. The hair thus washed is shiny, soft and is non-electric.

EXAMPLE 49

An aqueous solution having the following composition is prepared:

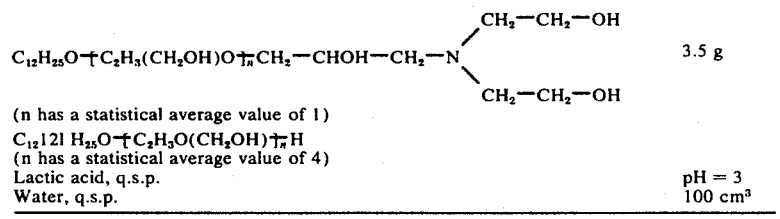
3.5 g (n has a statistical average value of 1)
C₁₂l2l H₂₅O——C₂H₃O(CH₂OH)ₙH
(n has a statistical average value of 4)
Lactic acid, q.s.p.           pH = 3
Water, q.s.p.             100 cm³

10 cm³ of this solution are applied to previously dampened hair and it is rubbed vigorously to emulsify all the dirt. It is thoroughly rinsed with water. Then another 8 to 10 cm³ of the above solution are applied. An abundant lather is obtained and the hair is rinsed. Hair thus washed is shiny, soft and non-electric.

EXAMPLE 50

An aqueous solution having the following composition is prepared:

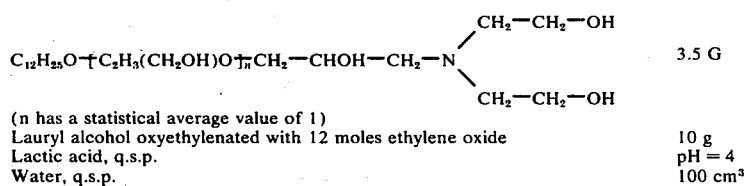
3.5 G (n has a statistical average value of 1)
Lauryl alcohol oxyethylenated with 12 moles ethylene oxide    10 g
Lactic acid, q.s.p.           pH = 4
Water, q.s.p.             100 cm³

10 cm³ of this solution are applied to previously dampened hair and it is rubbed vigorously to emulsify all the dirt. It is thoroughly rinsed with water. Then another 8 to 10 cm³ of the above solution are applied. An abundant lather is obtained and the hair is rinsed. Hair thus washed is shiny, soft and non-electric.

EXAMPLE 51

An aqueous solution having the following composition is prepared:

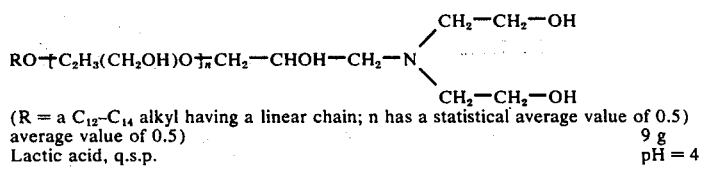

(R = a $C_{12}$–$C_{14}$ alkyl having a linear chain; n has a statistical average value of 0.5)
average value of 0.5)          9 g
Lactic acid, q.s.p.           pH = 4

| | |
|---|---|
| Water, q.s.p. | 100 cm³ |

10 cm³ of this solution are applied to previously dampened hair and it is rubbed vigorously to emulsify all the dirt. It is thoroughly rinsed with water. Then another 8 to 10 cm³ of the above solution are applied. An abundant lather is obtained and the hair is rinsed. Hair thus washed is shiny, soft and non-electric.

EXAMPLE 52

An aqueous solution having the following composition is prepared:

| | |
|---|---|
| $RO+C_2H_3(CH_2OH)O+_n CH_2-CHOH-CH_2-N \begin{smallmatrix} CH_2-CH_2-OH \\ \\ CH_2-CH_2-OH \end{smallmatrix}$ | 3 g |
| (R = a $C_{12}-C_{14}$ alkyl having a linear chain; n has a statistical average value of 0.5) | |
| $C_{12}H_{25}O+C_2H_3O(CH_2OH)+_n H$ | 9 g |
| (n has a statistical average value of 4) | |
| Lactic acid, q.s.p. | pH = 3 |
| Water, q.s.p. | 100 cm³ |

10 cm³ of this solution are applied to previously dampened hair and it is rubbed vigorously to emulsify all the dirt. It is thoroughly rinsed with water. Then another 8 to 10 cm³ of the above solution are applied. A generous lather is obtained and the hair is rinsed. Hair thus washed is shiny, soft and non-electric.

EXAMPLE 53

An aqueous solution having the following composition is prepared:

| | |
|---|---|
| $RO+C_2H_3(CH_2OH)O+_n CH_2-CHOH-CH_2-N \begin{smallmatrix} CH_2-CH_2-OH \\ \\ CH_2-CH_2-OH \end{smallmatrix}$ | 3 g |
| (R = a $C_{12}-C_{14}$ alkyl having a linear chain; n has a statistical average value of 0.5) | |
| Lauryl alcohol oxyethylenenated with 12 moles ethylene oxide | 12 g |
| Lactic acid, q.s.p. | pH = 4 |
| Water, q.s.p. | 100 cm³ |

10 cm³ of this solution are applied to previously dampened hair and it is rubbed vigorously to emulsify all the dirt. It is rinsed thoroughly with water. Then another 8 to 10 cm³ of the above solution are applied. A generous lather is obtained and the hair is rinsed. Hair thus washed is shiny, soft and non-electric.

EXAMPLE 54

An aqueous solution having the following composition is prepared:

| | |
|---|---|
| $RO+C_2H_3(CH_2OH)O+_n CH_2-CHOH-CH_2-N \begin{smallmatrix} CH_2-CH_2-OH \\ \\ CH_2-CH_2-OH \end{smallmatrix}$ | 9 g |
| (R = alkyl $C_{12}-C_{14}$; n has a statistical average value of 1) | |
| Lactic acid, q.s.p. | pH = 4 |
| Water, q.s.p. | 100 cm³ |

10 cm³ of this solution are applied to previously dampened hair and it is rubbed vigorously to emulsify all the dirt. It is thoroughly rinsed with water. Then another 8 to 10 cm³ of the above solution are applied. A generous lather is obtained and the hair is rinsed. Hair thus washed is shiny, soft and non-electric.

EXAMPLE 55

An aqueous solution having the following composition is prepared:

| | |
|---|---|
| $RO+C_2H_3(CH_2OH)O+_n CH_2-CHOH-CH_2-N \begin{smallmatrix} CH_2-CH_2-OH \\ \\ CH_2-CH_2-OH \end{smallmatrix}$ | 3.5 g |
| (R = alkyl $C_{12}-C_{14}$; n has a statistical average value of 1) | |
| $C_{12}H_{25}O+C_2H_3O(CH_2OH)+_n H$ | 8 g |
| (n has a statistical average value of 4) | |
| Lactic acid, q.s.p. | pH = 5 |

| | |
|---|---|
| -continued | |
| Water, q.s.p. | 100 cm³ |

10 cm³ of this solution are applied to previously dampened hair and it is rubbed vigorously to emulsify all the dirt. It is thoroughly rinsed with water. Then another 8 to 10 cm³ of the above solution are applied. A generous lather is obtained and the hair is rinsed. lather is obtained and the hair is rinsed. Hair thus washed is shiny, soft and non-electric.

EXAMPLE 57

The following composition is prepared:

| | |
|---|---|
| Nonylphenol oxyethylenated with 4 moles of ethylene oxide | 20 g |
| Nonylphenol oxyethylenated with 9 moles of ethylene oxide | 25 g |
| $R'O\text{-}[C_2H_3(CH_3)O]_m\text{-}[C_2H_3(CH_2OH)O]_n\text{-}CH_2\text{-}CHOH\text{-}CH_2\text{-}N\begin{array}{c}CH_2\text{-}CHOH\text{-}CH_3\\CH_2\text{-}CHOH\text{-}CH_3\end{array}$ | |
| ($R'$ = octadecyl, m has a statistical average value of 5.25 and n has a statistical average value of 1) | |
| Redistilled white olein | 2 g |
| Butylene glycol | 3 g |
| Propylene glycol | 17 g |
| 20% ammonia | 13 ml |
| Paratolylenediamine base | 1 g |
| Hydroquinone | 0.15 g |
| Pentasodium salt of diethylene traiamine pentacetic acid | 1.99 g |
| Sodium bisulfite, 35° Be' | 1.5 ml |
| Metadiaminoanisol sulfate | 0.07 g |
| Resorcinol | 0.47 g |
| Meta-aminophenol | 0.16 g |
| Para aminophenol base | 0.09 g |
| Nitroparaphenylenediamine | 0.0025 g |
| Water, q.s.p. | 100 ml |

Hair thus washed is shiny, soft and non-electric.

EXAMPLE 56

An aqueous solution having the following composition is prepared:

| | |
|---|---|
| $\left[RO\text{-}[C_2H_3(CH_2OH)O]_n\text{-}CH_2\text{-}CHOH\text{-}CH_2\text{-}\overset{+}{N}\begin{array}{c}CH_2\text{-}CH_2\text{-}OH\\ \\ CH_3CH_2\text{-}CH_2\text{-}OH\end{array}\right]SO_4CH_3^-$ | |
| ($R$ = alkyl $C_{12}$-$C_{14}$ having a linear chain; n has a statistical value of 0.5) | 9 g |
| Lactic acid, q.s.p. | pH = 3 |
| Water, q.s.p. | 100 cm³ |

10 cm³ of this solution is applied to previously dampened hair and it is vigorously rubbed to emulsify all the dirt. It is thoroughly rinsed with water. Then another 8 to 10 cm³ of the above solution are applied. A generous This is a clear oil. An equal volume of hydrogen peroxide at 20 volumes is added thereto. The resulting mixture forms a firm gel which is applied to 100% white hair and permitted to remain thereon for 30 minutes. Thereafter the hair is rinsed, shampooed and dried.

This dye completely covers the white hair which is as a result of the above treatment shiny, flexible, springy, non-electric and easy to manage.

EXAMPLE 58

The following composition is prepared:

| | |
|---|---|
| Nonylphenol oxyethylenated with 4 moles of ethylene oxide | 20 g |
| Nonylphenol oxyethylenated with 9 moles of ethylene oxide | 25 g |
| $R'O\text{-}[C_2H_3(CH_3)O]_m\text{-}[C_2H_3(CH_2OH)O]_n\text{-}CH_2\text{-}CHOH\text{-}CH_2\text{-}N\begin{array}{c}CH_2\text{-}CHOH\text{-}CH_3\\CH_2\text{-}CHOH\text{-}CH_3\end{array}$ | |
| ($R'$ = octadecyl, m has a statistical average value of 5.25 and n has a statistical average value of 1) | 2 g |
| Butylene glycol | 3 g |
| Propylene glycol | 17 g |
| 20% ammonia | 13 ml |
| Paratolylenediamine base | 1 g |
| Hydroquinone | 0.15 g |
| Pentasodium salt of diethylene triamine pentacetic acid | 1.99 g |
| Sodium bisulfate, 35° Be' | 1.5 ml |
| Metadiaminoanisol sulfate | 0.07 g |
| Resorcinol | 0.47 g |
| Meta-aminophenol | 0.16 g |
| Para-aminophenol base | 0.09 g |
| Nitroparaphenylenediamine | 0.0025 g |

| | |
|---|---|
| Water, q.s.p. | 100 ml |

This is a clear oil. An equal volume of hydrogen peroxide at 20 volumes is added thereto. The resulting mixture forms a firm gel which is applied to 100% white hair and is permitted to remain in contact therewith for 30 minutes. Thereafter the hair is rinsed, shampooed and dried. This dye completely covers the white hair which is as a result of this treatment flexible, springy, non-electric and easy to manage.

EXAMPLE 59

The following composition is prepared, which forms a clear oil:

| | |
|---|---|
| RO$-$[$C_2H_3O(CH_2OH)$]$_n$$-$H  (R = 9-octadecenyl and n has a statistical average value of 2) | 20 g |
| RO$-$[$C_2H_3O(CH_2OH)$]$_n$$-$H  (R = 9-octadecenyl and n has statistical value of 4) | 20 g |
| R'O$-$[$C_2H_3(CH_3)O$]$_m$$-$[$C_2H_3(CH_2OH)O$]$_n$$-$CH$_2$$-$CHOH$-$CH$_2$$-$N(CH$_2$$-$CHOH$-$CH$_3$)$_2$  (R' = octadecyl, m has a statistical average value of 5.25 and n has a statistical average value of 1) | 2 g |
| Redistilled white olein | 2 g |
| Butylene glycol | 8 g |
| Propylene glycol | 12 g |
| 20% ammonia | 13 ml |
| Paratolylenediamine base | 1 g |
| Hydroquinone | 0.15 g |
| Pentasodium salt of diethylene triamine pentacetic aicd | 1.99 g |
| Sodium bisulfite, 35° Be' | 1.5 g |
| Metadiaminoanisol sulfate | 0.07 g |
| Resorcinol | 0.47 g |
| Meta-aminophenol | 0.16 g |
| Para-aminophenol | 0.09 g |
| Nitroparaphenylenediamine | 0.0025 g |
| Water, q.s.p. | 100 ml |

An equal volume of hydrogen peroxide at 20 volumes is added to the above and the resulting mixture forms a firm gel which is applied to 100% white hair. This mixture is left on the hair for 30 minutes. Thereafter the hair is rinsed, shampooed and dried. The white hair is completely covered and is shiny, flexible, springy, non-electric and easy to manage.

EXAMPLE 60

The following composition is prepared, which forms a clear oil:

| | |
|---|---|
| RO$-$[$C_2H_3O(CH_2OH)$]$_n$$-$H  (R = 9-octadecenyl; n has a statistical average value of 2) | 20 g |
| RO$-$[$C_2H_3O(CH_2OH)$]$_n$$-$H  (R = 9-octadecenyl; n has a statistical average of 4) | 20 g |
| R'O$-$[$C_2H_3(CH_3)O$]$_m$$-$[$C_2H_3(CH_2OH)O$]$_n$$-$CH$_2$$-$CHOH$-$CH$_2$$-$N(CH$_2$$-$CHOH$-$CH$_3$)$_2$  (R' = octadecyl, m has a statistical average value of 5.25 and n has a statistical average value of 1) | 2 g |
| Butylene glycol | 8 g |
| Propylene glycol | 12 g |
| 20% ammonia | 13 ml |
| Paratolylenediamine base | 1 g |
| Hydroquinone | 0.15 g |
| Pentasodium salt of diethylene triamine pentacetic acid | 1.99 g |
| Sodium bisulfite, 35° Be' | 1.5 g |
| Metadiaminoanisol sulfate | 0.07 g |
| Resorcinol | 0.47 g |
| Meta-aminophenol | 0.16 g |
| Para-aminophenol | 0.09 g |
| Nitroparaphenylenediamine | 0.0025 g |
| Water, q.s.p. | 100 ml |

An equal volume of hydrogen peroxide at 20 volumes is added to the above and the resulting mixture forms a firm gel which is applied to 100% white hair. This mixture is left on the hair for 30 minutes. Thereafter the hair is rinsed, shampooed and dried. The white hair is completely covered and is flexible, shiny, springy, non-electric and easy to manage.

EXAMPLE 61

A shampoo having the following composition is prepared:

| | |
|---|---|
| RO$-$[$C_2H_3O(CH_2OH)$]$_n$$-$CH$_2$$-$CHOH$-$CH$_2$$-$N(morpholino)  R = a $C_{12}$-$C_{14}$ alkyl having a linear chain; n has a statistical average value of 1. | 6 g |

| | |
|---|---|
| $C_{12}H_{25}$—O—$(C_2H_3O(CH_2OH))_{\overline{n}}$H | 12 g |
| Lactic acid q.s.p. | pH 3 |
| Water q.s.p. | 100 g |

10 cm³ of this solution are applied to previously dampened hair and it is rubber vigorously to emulsify all the dirt. It is rinsed thoroughly with water. Then another 8 to 10 cm³ of the above solution are applied. A generous lather is obtained and the hair is rinsed. Hair thus washed is shiny, soft and non-electric.

EXAMPLE 62

A shampoo having the following composition is prepared:

4 g

RO—$(C_2H_3O(CH_2OH))_{\overline{n}}$CH$_2$—CHOH—CH$_2$—N⟨O⟩

R = a $C_{12}$–$C_{14}$ alkyl having a linear chain;
n has a statistical average value of 1.

| | |
|---|---|
| Lauryl alcohol oxyethylenated with 12 moles of ethylene oxide | 15 g |
| Lactic acid q.s.p. | pH 5 |
| Water q.s.p. | 100 g |

This shampoo is used and gives the same results as the shampoo of example 61.

EXAMPLE 63

A shampoo having the following composition is prepared:

RO—$(C_2H_3O(CH_2OH))_{\overline{n}}$CH$_2$—CHOH—CH$_2$—N⟨O⟩   5 g

R = a $C_{12}$–$C_{14}$ alkyl having a linear chain;
n has a statistical average value of 1.

| | |
|---|---|
| Lauryl alcohol oxyethylenated with 12 moles of ethylene oxide | 10 g |
| Lauryl diethanolamide | 4 g |
| Lactic acid q.s.p. | pH 6 |
| Water q.s.p. | 100 g |

This shampoo is used and gives the same results as the shampoo of example 61.

EXAMPLE 64

The following composition is prepared:

| | |
|---|---|
| Nonyl-phenol oxyethylenated with 4 moles of ethylene oxide | 26 g |
| Nonyl-phenol oxyethylenated with 9 moles of ethylene oxide | 22 g |
| $C_6H_{13}$\\$C_8H_{17}$/CH—CH$_2$O—$(C_2H_3O(CH_2OH))_{\overline{n}}$CH$_2$—CHOH—CH$_2$—N⟨O⟩ | 3 g |
| 96° Ethyl alcohol | 8 g |
| Propyleneglycol | 12 g |
| Ammonia 22° Baume | 12 ml |
| Dyes: | |
| Meta-diamino anisol sulfate | 0.030 g |
| Resorcine | 0.400 g |
| Meta-aminophenol base | 0.150 g |
| Para-aminophenol base | 0.087 g |
| Nitro-para-phenylene-diamine | 0.004 g |
| Para-toluylene-diamine | 1.000 g |
| Sodium salt of ethylene diamine tetracetic acid | 3 g |
| Sodium bisulfite d = 1.32 | 1.200 g |
| Water q.s.p. | 100 g |

This compound is mixed with its own volume of hydrogen peroxide at 20 volumes. The resulting gel when applied to hair with a paint-brush for 30 minutes gives after rinsing and drying a brown shade with a chestnut glint. The hair after treatment is very soft, silky and easy to manage.

EXAMPLES 65–66

The same composition is prepared as in example 64 except that $C_6H_{13}$\\$C_8H_{17}$/CH—CH$_2$O—$(C_2H_3O(CH_2OH))_{\overline{n}}$CH$_2$—CHOH—CH$_2$—N⟨O⟩   3 g is replaced:

for Example 65 by

RO—$(C_2H_3O(CH_2OH))_{\overline{n}}$CH$_2$—CHOH—CH$_2$—N⟨O⟩   3.5 g

R = 9-octadecenyl and for Example 66 by

-continued

| | |
|---|---|
| 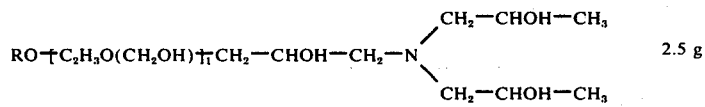 | 2.5 g |

Both of these compositions give the same results as the composition of example 64.

EXAMPLE 67

The following composition is prepared:

| | |
|---|---|
| Nonylphenol oxyethylenated with 4 moles of ethylene oxide | 24 g |
| Nonylphenol oxyethylenated with 9 moles of ethylene oxide | 24 g |
|  | 3 g |
| Diethanolamide of copra | 5 g |
| 96° Ethyl alcohol | 8 g |
| Propyleneglycol | 10 g |
| Ammonia 22° Baume | 12 ml |
| Para-aminophenol base | 0.080 g |
| Meta-aminoauisol sulfate | 0.025 g |
| Resorcine | 0.300 g |
| Meta-aminophenol base | 0.060 g |
| Nitro-paraphenylenediamine | 0.003 g |
| Hydroquinone | 0.170 g |
| Sodium salt of ethylene diamine tetracetic acid | 3 g |
| Sodium bisulfite d = 1.32 | 0.800 g |
| Para-toluylenediamine | 1.050 g |
| Water q.s.p. | 100 g |

This compound is mixed with its own volume of hydrogen peroxide at 20 volumes. The resulting gel when applied to hair with a paint-brush for 30 minutes gives after rinsing and drying a dark chestnut shade with a light chestnut glint. The hair after treatment is very soft silky and easy to manage.

EXAMPLE 68

The following composition is prepared:

| | |
|---|---|
| Nonylphenol oxyethylenated with 4 moles of ethylene oxide | 22 g |
| Nonylphenol oxyethylenated with 9 moles of ethylene oxide | 25 g |
| Oleic acid | 4 g |
| 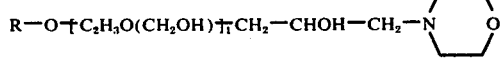 | 4 g |
| R represents an alkyl radical having 12 to 18 carbon atoms | |
| Butylglycol | 3 g |
| Propyleneglycol | 17 g |
| Ammonia 22° Baume | 12 ml |
| Dyes: | |
| Resorcine | 0.040 g |
| Meta-aminophenol base | 0.060 g |
| Para aminophenol base | 0.280 g |
| Nitro-paraphenylenediamine | 0.020 g |
| Para-toluylenediamine | 0.120 g |
| Hydroquinone | 0.170 g |
| Sodium salt of ethylene diamine tetracetic acid | 3 g |
| Sodium bisulfite d = 1.32 | 0.800 g |
| Water q.s.p. | 100 g |

This compound is mixed with its own volume of hydrogen peroxide at 20 volumes. The resulting gel when applied to hair with a paint-brush for 30 minutes gives after rinsing and drying a light chestnut shade with a golden fair shade. The hair after treatment is very soft, silky and easy to manage.

EXAMPLE 69

The same composition is prepared as in example 68 except that

| | |
|---|---|
| 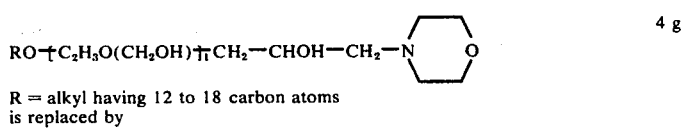 | 4 g |
| R = alkyl having 12 to 18 carbon atoms is replaced by | |

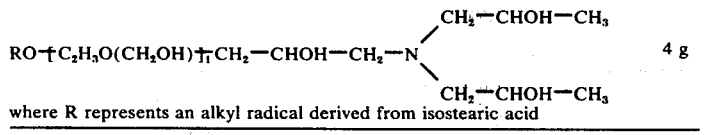

wherein R represents an alkyl radical derived from isostearic acid.

This composition gives the same results as the composition of example 68.

EXAMPLE 70

The following composition is prepared:

| | |
|---|---|
| Cetyl-stearyl alcohol | 20 g |
| Oleyl diethanolamide | 4 g |
| Cetyl-stearyl sodium sulfate | 5 g |
| RO—$[C_2H_3O(CH_2OH)]_{\overline{10.9}}$—$CH_2$—CHOH—$CH_2$—N(CH$_2$—CH$_2$—OH)(CH$_2$—CH$_2$—OH) | 4 g |
| wherein R = cetyl-stearyl | |
| Ammonia 22° Baume | 12 ml |
| Dyes: | |
| Meta diamino-anisol sulfate | 0.048 g |
| Resorcine | 0.420 g |
| Meta-aminophenol base | 0.150 g |
| Nitro-paraphenylenediamine | 0.085 g |
| Para-tolylenediamine | 0.004 g |
| Sodium salt of ethylene diamine tetracetic acid | 1 g |
| Sodium bisulfite d = 1.32 | 1.200 g |
| Water q.s.p. | 100 g |

30 g of this composition are mixed with 45 g of hydrogen peroxide at 20 volumes. A smooth, firm cream is obtained which sticks to the hair and is pleasant to use. When applied to 100% gray hair, the result, after shampooing, is a fair shade. The hair, after treatment is bright, has a silky touch and is easy to manage.

EXAMPLE 71

The same composition is prepared as in example 70 except that

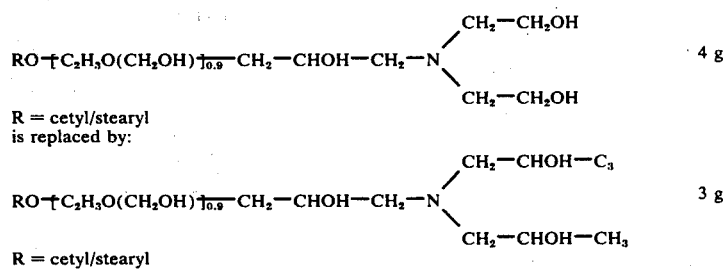

This composition gives the same results as the composition of example 70.

EXAMPLE 72

The following composition is prepared:

| | |
|---|---|
| 1,8-Bis-γ-aminopropylamino anthraquinone | 0.15 g |
| 1-diethylamino 2-ethylamino-nitro-4-NN-dihydroxyethylamino benzene dihydrochloride | 0.6 g |
| 4-N-methylamino-3-nitro-1-N-β-aminoethylamino benzene | 0.25 g |
| [γ-hydroxy-4 (γ-methylmorpholinium) propylamino anthraquinone] methyl sulfate | 0.1 g |
| 2-β-aminoethylamino- anthraquinone | 0.2 g |
| 1,5-di-(β-aminopropylamino) anthraquinone | 0.3 g |
| 1-dimethylamino-3-amino ethylamino-4-nitro benzene | 0.3 g |
| 1-methylamino-4-amino propylamino anthraquinone | 0.3 g |
| 1-amino propylamino-anthraquinone | 0.15 g |
| 1,4-diamino-5-γ-aminopropylamino-anthraquinone | 0.4 g |
| 3-nitro-4-β-aminoethylamino-anisole, monohydrochloride | 0.2 g |
| RO—$[C_2H_3O(CH_2OH)]_{\overline{15}}$CH$_2$—CHOH—CH$_2$—N(CH$_2$—CH$_2$OH)(CH$_2$—CH$_2$OH) (I) | 4 g |
| R = nonylphenyl | |
| diethanolamide of copra | 4 g |
| "Trilon X100" (iso octyl phenol with 10 moles of ethylene | |

-continued

| | |
|---|---|
| 3-amyloxy-1,2-propane diol | 3 g |
| butylglycol | 6 g |
| monoethanolamine q.s.p. | pH 9.5 |
| water q.s.p. | 100 g |

This composition is applied as a shampoo for 20 to 30 minutes on chestnut hair with 30 to 70% gray hair. After rinsing a uniform dark chestnut shade is obtained masking the gray hair.

The presence of the compound (I) according to the present application improves the uniformity of the shade on permanent waved hair and permits a pleasant use.

EXAMPLE 73

The following hair rinse composition is prepared:

| | |
|---|---|
| Copolymer of vinyl pyrrolidone and vinyl acetate 60:40 (PVP/VA S 630 of GAF Corp. New-York NY) | 2 g |
| Ethyl alcohol q.s.p. | 20° |
| RO [C$_2$H$_3$O(CH$_2$OH)$_{0.5}$] CH$_2$—CHOH—CH$_2$—N$\underset{CH_2-CH_2OH}{\overset{CH_2-CH_2OH}{\diagup\diagdown}}$ wherein R is an alkyl having 12 to 14 carbon atoms | 0.5 g |
| Perfume | 0.2 g |
| Water q.s.p. | 100 cc |

A direct dye may be added to this composition.

After shampooing rinsing and wiping, 20 ml of this composition are applied to the hair which is then permanently waved and dried.

EXAMPLE 74

| | |
|---|---|
| Copolymer of vinyl acetate and crotonic acid (MW 20,000) (Resin 28 1310 of National Starch and Chemical Corp. New York NY) | 1.5 g |
| Aminomethyl propane diol q.s.p. | pH 8.5 |
| Ethyl alcohol q.s.p. | 50° |
| RO [C$_2$H$_3$O(CH$_2$OH)]$_1$ CH$_2$—CHOH—CH$_2$—N$\underset{CH_2-CH_2}{\overset{CH_2-CH_2}{\diagup\diagdown}}$O wherein R represents an alkyl radical having 12 to 14 carbon atoms | 0.6 g |
| Perfume | 0.2 g |
| Water q.s.p. | 100 cc |

After shampooing rinsing and wiping, 20 ml of this composition are applied to the hair which is then permanently waved and dried.

EXAMPLE 75

| | |
|---|---|
| Copolymer of vinyl acetate and crotonic acid (MW:20 000) (Resin 28 1310 of National Starch and Chemical Corp., New York NY) | 1.2 g |
| Aminoethyl propanol q.s.p. | pH 7 |
| Ethyl alcohol q.s.p. | 50° |
| Copolymer of vinylpyrrolidone and vinyl acetate 60:40 (PVP / VA S 630 of GAF Corp. New York NY) | 0.5 g |
| $\underset{C_{10}H_{21}}{\overset{C_8H_{17}}{\diagdown\diagup}}$CH—CH$_2$O—[C$_2$H$_3$O(CH$_2$OH)]$_1$ CH$_2$—CHOH—CH$_2$—N$\underset{CH_2-CH_2}{\overset{CH_2-CH_2}{\diagup\diagdown}}$O | |
| Perfume | 0.2 g |
| A direct dye may be added to this composition. | |
| Water q.s.p. | 100 cc |

After shampooing rinsing and wiping, 20 ml of this composition are applied to the hair which is then permanently waved and dried.

EXAMPLE 76

| | |
|---|---|
| Monobutyl ester of the copolymer methyl vinyl ether and maleic acid (50% solution) | 3 g |

-continued

| | |
|---|---|
| (Resin Gantrez ES 425 of GAF Corp. New-York NY) | |
| Triethanolamine q.s.p. | pH 7 |
| Ethyl alcohol q.s.p. | 50° |
| 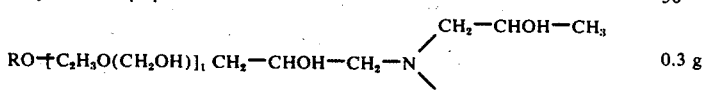 | 0.3 g |
| wherein R represents a hydrocarbon radical derived from isostearic acid | |
| Perfume | 0.3 g |
| A direct dye may be added to this composition. | |
| Water q.s.p. | 100 cc |

After shampooing rinsing and wiping, 20 ml of this composition are applied to the hair which is then permanently waved and dried.

What is claimed is:

1. A cosmetic composition for treating the hair comprising an aqueous solution of a cationic surface active agent selected from the group consisting of 1. a mixture of compounds having the formula

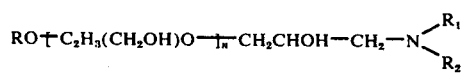

wherein R is selected from the group consisting of alkyl having 8–22 carbon atoms, alkenyl having 8–22 carbon atoms and alkyl phenyl having 8–22 carbon atoms, $R_1$ and $R_2$ each independently are selected from the group consisting of lower alkyl having 1–4 carbon atoms and hydroxy lower alkyl having 1–4 carbon atoms or together with the nitrogen atom to which they are attached form a ring selected from the group consisting of morpholine and piperidine, and n has a statistical average value of 0.5–10 and 2. a mixture of compounds which are the quaternary ammonium salts of (1) having the formula

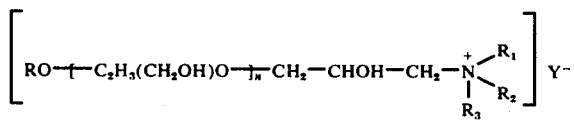

wherein R, $R_1$, $R_2$ and n have the meanings given above, $R_3$ is selected from the group consisting of methyl and ethyl and Y is an anion selected from the group consisting of Cl, Br, I, $SO_4CH_3$, $SO_4C_2H_5$, $CH_3SO_3$ and

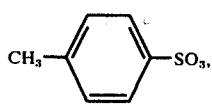

said cationic surface active agent being present in amounts of about 0.1 to 10 percent by weight thereof.

2. The cosmetic composition of claim 1 also including an organic acid in amounts effective to provide a pH of about 3 to 6.5.

3. The cosmetic composition of claim 2 wherein said organic acid is selected from the group consisting of lactic, acetic and citric acid.

4. A cosmetic composition for treating the hair comprising an aqueous solution of a cationic surface-active agent selected from the group consisting of 1. a mixture of compounds having the formula

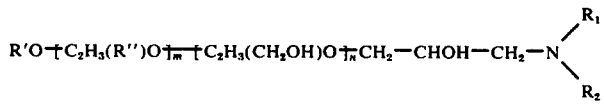

wherein R' is selected from the group consisting of alkyl having 12–20 carbon atoms and alkenyl having 12–20 carbon atoms, R" is selected from the group consisting of methyl and ethyl, m has a statistical average value of 2–6, $R_1$ and $R_2$ each independently are selected from the group consisting of lower alkyl having 1–4 carbon atoms and hydroxy lower alkyl having 1–4 carbon atoms or together with the nitrogen atom to which they are attached form a ring selected from the group consisting of morpholine and piperidine and n has a statistical average value of 0.5–4 and 2. a mixture of compounds which are the quaternary ammonium salts of (1) having the formula

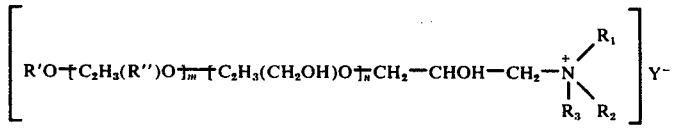

wherein R', R", $R_1$, $R_2$, m and n have the meanings given above, $R_3$ is selected from the group consisting of methyl and ethyl and Y is an anion selected from the group consisting of Cl, Br, I, $SO_4CH_3 SO_4C_2H_5$, $CH_3SO_3$ and

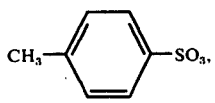

said surface active agent being present in amounts of about 0.1 to 6 percent by weight thereof.

5. The cosmetic composition of claim 4 also including an organic acid in amounts effective to provide a pH of about 3 to 6.5.

6. The cosmetic composition of claim 5 wherein said organic acid is selected from the group consisting of lactic, acetic and citric acid.

7. The cosmetic composition of claim 1 also including a cosmetic resin in amounts of about 0.5 to 5%.

8. The cosmetic composition of claim 7 wherein said cosmetic resin is selected from the group consisting of polyvinyl pyrrolidone, a copolymer of vinyl pyrrolidone and vinyl acetate, a copolymer of crotonic acid and vinyl acetate, and a monoalkyl ester of a copolymer of methyl vinyl ether and maleic acid.

9. The cosmetic composition of claim 8 also including a lower alkanol in amounts of about 15 to 60% by weight of said solution.

10. The cosmetic composition of claim 9 wherein said lower alkanol is selected from the group consisting of ethanol and isopropanol.

11. The composition of claim 10 containing 0.1 to 2% of said cationic surface-active agent.

12. The cosmetic composition of claim 4 also including a cosmetic resin in amounts of about 0.5 to 5%.

13. The cosmetic composition of claim 12 wherein said cosmetic resin is selected from the group consisting of polyvinyl pyrrolidone, a copolymer of vinyl pyrrolidone and vinyl acetate, a copolymer of crotonic acid and vinyl acetate, and a monoalkyl ester of a copolymer of methyl vinyl ether and maleic acid.

14. The cosmetic composition of claim 13 also including a lower alkanol in amounts of about 15 to 60% by weight of said solution.

15. The cosmetic composition of claim 14 wherein said lower alkanol is selected from the group consisting of ethanol and isopropanol.

16. The composition of claim 15 containing 0.1 to 2% of said cationic surface active agent.

17. The cosmetic composition of claim 16 also containing a perfume in amounts of about 0.05 to 0.5%.

18. The cosmetic composition of claim 16 having a pH of 7 to 8.5.

19. The cosmetic composition of claim 11 having a pH of 7 to 8.5.

* * * * *